(12) United States Patent
Sasaki

(10) Patent No.: US 6,995,110 B2
(45) Date of Patent: Feb. 7, 2006

(54) COMPLEX CATALYST, PROCESS FOR PRODUCING THE COMPLEX CATALYST, AND PROCESS FOR PRODUCING ALCOHOL DERIVATIVE WITH THE COMPLEX CATALYST

(75) Inventor: Kazuaki Sasaki, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 124 days.

(21) Appl. No.: 10/471,103

(22) PCT Filed: Apr. 17, 2002

(86) PCT No.: PCT/JP02/03791

§ 371 (c)(1),
(2), (4) Date: Sep. 8, 2003

(87) PCT Pub. No.: WO02/085516

PCT Pub. Date: Oct. 31, 2002

(65) Prior Publication Data

US 2004/0077487 A1  Apr. 22, 2004

(30) Foreign Application Priority Data

| Apr. 18, 2001 | (JP) | ............................. | 2001-119307 |
| Sep. 28, 2001 | (JP) | ............................. | 2001-300868 |
| Sep. 28, 2001 | (JP) | ............................. | 2001-300869 |
| Sep. 28, 2001 | (JP) | ............................. | 2001-300870 |

(51) Int. Cl.
*B01J 31/00* (2006.01)
(52) U.S. Cl. .................................................. 502/171
(58) Field of Classification Search ................. 502/171
See application file for complete search history.

(56) References Cited

U.S. PATENT DOCUMENTS

| 5,110,962 A | 5/1992 | Cahiez et al. |
| 2003/0216250 A1 | 11/2003 | Kim et al. |

FOREIGN PATENT DOCUMENTS

| JP | 5-59718 B2 | 8/1993 |
| JP | 11-209387 A | 8/1999 |
| JP | 2000-26442 A | 1/2000 |
| WO | WO 96/28402 A1 | 9/1996 |
| WO | WO 00/00525 A | 1/2000 |
| WO | WO 00/09463 A1 | 2/2000 |

OTHER PUBLICATIONS

J. Ready et al., "Asymmetric Catalytic Synthesis of α-Aryloxy Alcohols: Kinetic Resolution of Terminal Epoxides via Highly Enantioselective Ring-Opening with Phenois", J. Am. Chem. Society, (1999), 121, pp. 6086-6087.
Q. Mingxing et al., "Ethylene oligomerization by diimine iron(II) complexes/EAO", *Journal of Molecular Catalysis A: Chemical*, vol. 160, 2000, XP-002291190, pp. 243-247.
Patent Abstracts of Japan, vol. 0151, No. 63-(C-0826,Apr. 24, 1991, corresponding to JP-A 03-03451 published Feb. 14, 1991, to Sumitomo Chemical Co.
J.M. Ready et al., "Highly Active Oligomeric (salen)Co Catalysts for Asymmetric Epoxide Ring-Opening Reactions", *J. Am. Chem. Soc.*, vol. 123, 2001, pp. 2687-2688.

*Primary Examiner*—Taofiq Solola
(74) *Attorney, Agent, or Firm*—Sughrue Mion, PLLC

(57) ABSTRACT

There are provided (asymmetric) complex catalysts comprising metal complexes and Lewis acids as components, the metal complex being of formula (1):

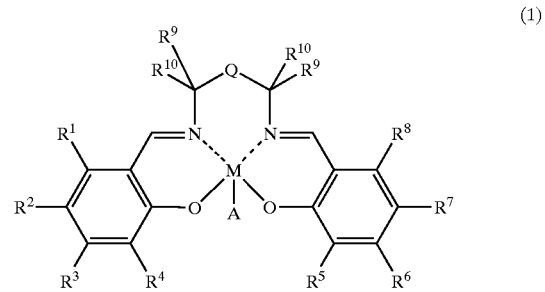

wherein $R^1$, $R^2$, $R^3$, $R^4$, $R^5$, $R^6$, $R^7$ and $R^8$ are the same or different and are independently hydrogen, halogen, alkyl or the like; one of $R^9$ and $R^{10}$ is hydrogen and the other is alkyl of 1 to 4 carbon atoms or the like; Q is a single bond or alkylene of 1 to 4 carbon atoms; M is a metal ion; and A is a balancing counter ion or ligand; processes for the production of these complex catalysts; processes for the production of (optically active) alcohol derivatives, characterized in that cyclic ether compounds are reacted with phenol derivatives in the presence of these complex catalysts; and further processes for producing (optically active) nitrogen-containing heterocyclic compounds by reacting these alcohol derivatives with halogenated nitrogen-containing heterocyclic compounds in the presence of a base.

10 Claims, No Drawings

COMPLEX CATALYST, PROCESS FOR PRODUCING THE COMPLEX CATALYST, AND PROCESS FOR PRODUCING ALCOHOL DERIVATIVE WITH THE COMPLEX CATALYST

TECHNICAL FIELD OF INVENTION

The present invention relates to a process for the production of alcohol derivatives and more particularly to a process for the regio- or stereo-selective production of alcohol derivatives as well as to catalysts having excellent regio- and stereo-selectivity.

BACKGROUND ART

It has been known that 2-[1-methyl-2-(4-phenoxyphenoxy)ethoxy]-pyridine, which is a nitrogen-containing heterocyclic compound having juvenile hormone activity, is produced by a process in which an alcohol derivative such as 1-methyl-2-(4-phenoxyphenoxy)ethanol is reacted with a halogenated nitrogen-containing heterocyclic compound such as 2-chloropyridine in the presence of a base (JP 3034951 A). The alcohol derivative, 1-methyl-2-(4-phenoxyphenoxy)ethanol, which is an intermediate for production, has been produced by, for example, reacting propylene oxide with 4-phenoxyphenol in the presence of a base. In this process, however, in addition to the desired 1-methyl-2-(4-phenoxyphenoxy)ethanol, there is also produced its isomer, 2-methyl-2-(4-phenoxyphenoxy)ethanol, as a by-product; therefore, it is necessary to separate and remove this isomer by a separating technique such as crystallization. For this reason, the above process cannot always be said to be a quite satisfactory process from an industrial point of view.

Further, for producing optically active nitrogen-containing heterocyclic compounds, it requires the step of treating an organic carboxylic acid ester of the above alcohol derivative with a microorganism-derived esterase to cause asymmetric hydrolysis, affording an optically active alcohol derivative. This cannot always be said to be quite satisfactory from an industrial point of view in that the number of steps for production becomes increased.

PURPOSE OF THE INVENTION

The primary purpose of the invention is to provide an industrially advantageous process for the production of alcohol derivatives as described above.

SUMMARY OF THE INVENTION

According to the process of the present invention, an alcohol derivative can be obtained in a regio- and stereo-selective manner by the use of a catalyst as described below for the reaction of a cyclic ether compound, a typical example of which is propylene oxide, with a phenol derivative. In addition, by reacting the alcohol derivative obtained by this process with a halogenated nitrogen-containing heterocyclic compound, the desired nitrogen-containing heterocyclic compound can be produced in high yield.

That is, the present invention provides:

1. a complex catalyst comprising a metal complex and a Lewis acid as components, the metal complex being of formula (1):

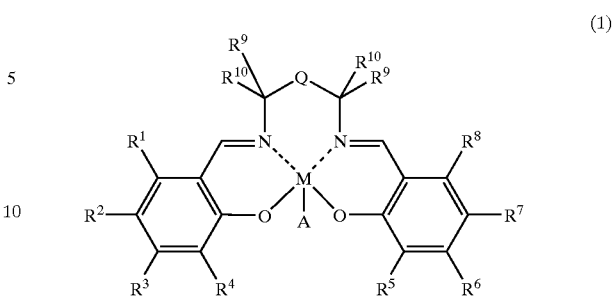

wherein $R^1$, $R^2$, $R^3$, $R^4$, $R^5$, $R^6$, $R^7$ and $R^8$ are the same or different and are independently hydrogen, halogen, alkyl, alkenyl, alkynyl, alkoxy, haloalkyl, haloalkoxy, hydroxyl, nitro, amino, carbamoyl, carboxyl, substituted or unsubstituted aryl, or silyl; or two adjacent groups of $R^1$, $R^2$, $R^3$, $R^4$, $R^5$, $R^6$, $R^7$ and $R^8$ are combined together to represent a naphthalene ring by forming a ring together with a benzene ring to which they are attached;

one of $R^9$ and $R^{10}$ is hydrogen and the other is phenyl or naphthyl optionally substituted with at least one selected from the group consisting of alkyl of 1 to 4 carbon atoms, alkoxy of 1 to 4 carbon atoms, haloalkyl, haloalkoxy and halogen; or either one pair of $R^9$ and $R^{10}$ attached to the different carbon atoms are combined together at their ends to form a tetramethylene linkage and the other pair are hydrogen atoms;

Q is a single bond or alkylene of 1 to 4 carbon atoms; or Q is combined with $R^9$ and $R^{10}$ to represent 1,1'-binaphthyl attached to the nitrogen atoms at 2 and 2' positions;

M is a metal ion; and

A is a balancing counter ion or ligand;

2. a process for the production of the above complex catalyst;

3. a process for the production of an alcohol derivative, characterized in that a cyclic ether compound is reacted with a phenol derivative in the presence of the above complex catalyst; and 4. the above production process comprising the step of reacting the alcohol derivative with a halogenated nitrogen-containing heterocyclic compound in the presence of a base to give a nitrogen-containing heterocyclic compound.

DETAILED DESCRIPTION OF THE INVENTION

First, the following will describe the metal complex catalyst of formula (1).

In the above formula (1), the halogen atom and the alkyl, alkenyl, alkynyl, alkoxy, haloalkyl, haloalkoxy, hydroxyl, nitro, amino, carbamoyl, carboxyl, aryl and silyl groups, which are represented by $R^1$, $R^2$, $R^3$, $R^4$, $R^5$, $R^7$ and $R^8$, are defined below.

The halogen atom may include fluorine, chlorine, bromine and the like.

The alkyl group may include straight chain, branched chain or cyclic alkyl groups of 1 to 6 carbon atoms, such as methyl, ethyl, n-propyl, isopropyl, n-butyl, isobutyl, sec-butyl, tert-butyl, n-pentyl, tert-pentyl, n-hexyl, cylcopentyl and cyclohexyl.

The alkoxy group may include straight chain, branched chain or cyclic alkoxy groups of 1 to 6 carbon atoms, such as methoxy, ethoxy, n-propoxy, isopropoxy, n-butoxy, isobutoxy, sec-butoxy, tert-butoxy, n-hexyloxy and cyclohexyloxy.

The haloalkyl group may include those obtained by substituting the above halogen atom(s) for one or more than one hydrogen atom of the above alkyl, such as chloromethyl, chloroethyl, fluoromethyl and trifluoromethyl.

The haloalkoxy group may include those obtained by substituting the above halogen atom(s) for one or more than one hydrogen atom of the above alkoxy, such as chloromethoxy, chloroethoxy, fluoroethoxy and trifluoromethoxy.

The alkenyl group may include straight chain, branched chain or cyclic alkenyl groups of 2 to 6 carbon atoms, such as vinyl, propenyl, 1-butenyl, 2-butenyl, 2-methyl-1-propenyl, pentenyl, hexenyl and cyclohexenyl.

The alkynyl group may include straight chain or branched chain alkynyl groups of 2 to 6 carbon atoms, such as ethynyl, propynyl, 1-butynyl, 2-butynyl and hexynyl.

The substituted or unsubstituted aryl group may include aryl groups optionally substituted with methyl, nitro or methoxy, such as phenyl, toluyl, xylyl, nitrophenyl, methoxyphenyl and naphthyl.

The silyl group may include silyl groups tri-substituted with hydrocarbon groups, and the hydrocarbon groups may include $C_{1-4}$ alkyl or aryl. Specific examples thereof may include trimethylsilyl, triethylsilyl, triphenylsilyl and tert-butyldimethylsilyl.

Two adjacent groups of $R^1$, $R^2$, $R^3$, $R^4$, $R^5$, $R^6$, $R^7$ and $R^8$ are combined together to represent a naphthalene ring together with a benzene ring to which they are attached.

In the above formula (1), one of $R^9$ and $R^{10}$ is hydrogen and the other is phenyl or naphthyl optionally substituted with at least one selected from the group consisting of $C_{1-4}$ alkyl, $C_{1-4}$ alkoxy, haloalkyl where the alkyl group is halogenated, haloalkoxy where the alkoxy group is halogenated, and halogen. Alternatively, either one pair of $R^9$ and $R^{10}$ attached to the different carbon atoms are combined together to form a tetramethylene linkage. In this case, the other pair are hydrogen atoms.

The $C_{1-4}$ alkyl group may include straight chain or branched chain alkyl groups such as methyl, ethyl, n-propyl, isopropyl, n-butyl and tert-butyl.

The $C_{1-4}$ alkoxy group may include straight chain or branched chain alkoxy groups such as methoxy, ethoxy, n-propoxy, isopropoxy, n-butoxy and tert-butoxy.

The halogen atom may include fluorine, chlorine, bromine and the like. The phenyl or naphthyl group optionally substituted with at least one selected from the group consisting of $C_{1-4}$ alkyl, $C_{1-4}$ alkoxy, haloalkyl, haloalkoxy and halogen may include phenyl, 1-naphthyl, 2-naphthyl, 2-methylphenyl, 3-methylphenyl, 4-methylphenyl, 2-methoxyphenyl, 3-methoxyphenyl, 4-methoxyphenyl, 2-chlorophenyl, 3-chlorophenyl, 4-chlorophenyl, 2-fluorophenyl, 3-fluorophenyl, 4-fluorophenyl, 4-bromophenyl, 2-trifluoromethylphenyl, 3-trifluoromethylphenyl and 4-trifluoromethylphenyl.

The alkylene group of 2 to 4 carbon atoms, which is represented by Q, may include methylene, ethylene, trimethylene and tetramethylene.

In the above formula (1), M is a metal ion and A is a balancing counter ion or ligand. For example, when the ionic valence of a metal ion is equal to the coordination number of ligands, A is not present. When the ionic valence of a metal ion is different from the coordination number, A is a counter ion or ligand.

The metal ion may include cobalt ion, chromium ion and manganese ion. The counter ion or ligand may include halogen ions such as chloride ion, perfluoroalkoxide ions such as nonafluoro-tert-butoxide ion, acetate ligands, and phenolate ligands corresponding to phenol derivatives, which are used in the reaction of cyclic ether compounds with phenol derivatives as described below. In particular, preferred are acetate ligands and phenolate ligands corresponding to phenol derivatives, which are used in the reaction of cyclic ether compounds with phenol derivatives as described below.

In the present specification, the halogen atom and the alkyl, alkylene, alkenyl, alkynyl and aryl groups found in the compounds of formulas (2) to (6') refer to the same as described above, unless otherwise indicated.

The above metal complexes of formula (1) may include the following metal complexes of formula (1a), optically active metal complexes of formula (1') and optically active metal complexes of formula (1'a).

More specifically, the metal complexes of formula (1a) corresponding to the above formula (1) wherein Q is a single bond:

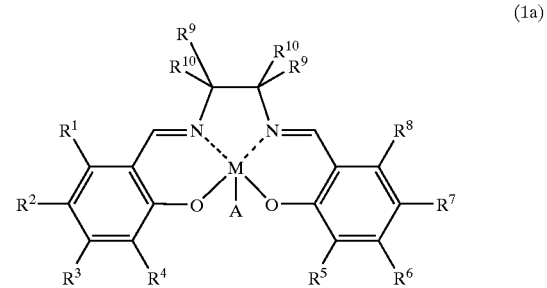

(1a)

wherein $R^1$, $R^2$, $R^3$, $R^4$, $R^5$, $R^6$, $R^7$, $R^8$, $R^9$, $R^{10}$, M and A are as defined above.

Further, the optically active metal complexes of formula (1'):

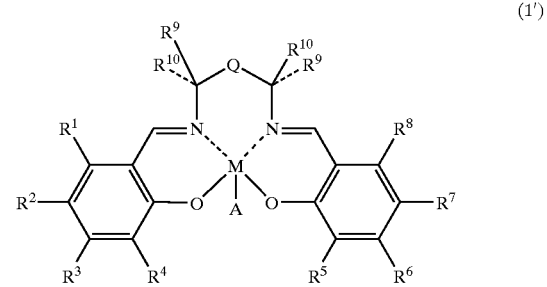

(1')

wherein $R^1$, $R^2$, $R^3$, $R^4$, $R^5$, $R^6$, $R^7$, $R^8$, $R^9$, $R^{10}$, M, A and Q are as defined above.

The optically active metal complexes of the following formula (1'a) corresponding to the above formula (1') wherein Q is a single bond:

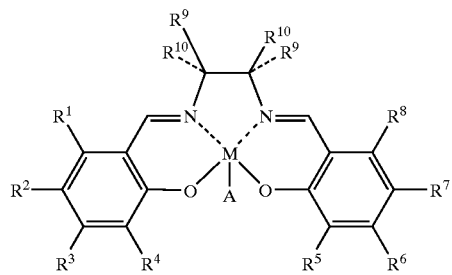

wherein $R^1$, $R^2$, $R^3$, $R^4$, $R^5$, $R^6$, $R^7$, $R^8$, $R^9$, $R^{10}$, M and A are as defined above.

The metal complexes of formula (1) or (1a) may include:
N,N'-bis(salicylidene)-1,2-ethylenediamino cobalt (III) acetate,
N,N'-bis(salicylidene)-1,2-ethylenediamino cobalt (III) 4-phenoxyphenolate,
N,N'-bis(3,5-di-tert-butylsalicylidene)-1,2-cyclohexanediamino cobalt (III) acetate,
N,N'-bis(3,5-di-tert-butylsalicylidene)-1,2-cyclohexanediamino cobalt (III) nonafluoro-tert-butoxide,
N,N'-bis(3,5-di-tert-butylsalicylidene)-1,2-cyclohexanediamino cobalt (III) hexafluoroisopropoxide,
N,N'-bis(3,5-di-tert-butylsalicylidene)-1,2-cyclohexanediamino cobalt (III) 4-phenoxyphenolate,
N,N'-bis(3,5-di-tert-pentylsalicylidene)-1,2-cyclohexanediamino cobalt (III) acetate,
N,N'-bis(3,5-di-tert-pentylsalicylidene)-1,2-cyclohexanediamino cobalt (III) nonafluoro-tert-butoxide,
N,N'-bis(3,5-di-tert-pentylsalicylidene)-1,2-cyclohexanediamino cobalt (III) hexafluoroisopropoxide,
N,N'-bis(3,5-di-tert-pentylsalicylidene)-1,2-cyclohexanediamino cobalt (III) 4-phenoxyphenolate,
N,N'-bis(salicylidene)-1,2-cyclohexanediamino cobalt (III) acetate,
N,N'-bis(salicylidene)-1,2-cyclohexanediamino cobalt (III) nonafluoro-tert-butoxide,
N,N'-bis(salicylidene)-1,2-cyclohexanediamino cobalt (III) 4-phenoxyphenolate,
N,N'-bis(3-tert-butyl-5-methylsalicylidene)-1,2-cyclohexanediamino cobalt (III) acetate,
N,N'-bis(3-tert-butyl-5-methylsalicylidene)-1,2-cyclohexanediamino cobalt (III) nonafluoro-tert-butoxide,
N,N'-bis(3-tert-butyl-5-methylsalicylidene)-1,2-cyclohexanediamino cobalt (III) 4-phenoxyphenolate,
N,N'-bis(3-tert-butyl-5-nitrosalicylidene)-1,2-cyclohexanediamino cobalt (III) acetate,
N,N'-bis(3-tert-butyl-5-nitrosalicylidene)-1,2-cyclohexanediamino cobalt (III) nonafluoro-tert-butoxide,
N,N'-bis(3-tert-butyl-5-nitrosalicylidene)-1,2-cyclohexanediamino cobalt (III) 4-phenoxyphenolate,
N,N'-bis(3-tert-butyl-5-methoxysalicylidene)-1,2-cyclohexanediamino cobalt (III) acetate,
N,N'-bis(3-tert-butyl-5-methoxysalicylidene)-1,2-cyclohexanediamino cobalt (III) nonafluoro-tert-butoxide,
N,N'-bis(3-tert-butyl-5-methoxysalicylidene)-1,2-cyclohexanediamino cobalt (III) 4-phenoxyphenolate,
N,N'-bis(3-tert-butyl-5-chlorosalicylidene)-1,2-cyclohexanediamino cobalt (III) acetate,
N,N'-bis(3-tert-butyl-5-chlorosalicylidene)-1,2-cyclohexanediamino cobalt (III) nonafluoro-tert-butoxide,
N,N'-bis(3-tert-butyl-5-chlorosalicylidene)-1,2-cyclohexanediamino cobalt (III) 4-phenoxyphenolate,
N,N'-bis(3-tert-butylsalicylidene)-1,2-cyclohexanediamino cobalt (III) acetate,
N,N'-bis(3-tert-butylsalicylidene)-1,2-cyclohexanediamino cobalt (III) nonafluoro-tert-butoxide,
N,N'-bis(3-tert-butylsalicylidene)-1,2-cyclohexanediamino cobalt (III) 4-phenoxyphenolate,
N,N'-bis[(5-methyl-3-(1-methyl-1-phenylethyl)salicylidene)-1,2-cyclohexanediamino cobalt (III) acetate,
N,N'-bis[(5-methyl-3-(1-methyl-1-phenylethyl)salicylidene)-1,2-cyclohexanediamino cobalt (III) nonafluoro-tert-butoxide,
N,N'-bis[(5-methyl-3-(1-methyl-1-phenylethyl)salicylidene)-1,2-cyclohexanediamino cobalt (III) 4-phenoxyphenolate,
N,N'-bis(3-tert-butyl-5-triphenylmethylsalicylidene)-1,2-cyclohexanediamino cobalt (III) acetate,
N,N'-bis(3-tert-butyl-5-triphenylmethylsalicylidene)-1,2-cyclohexanediamino cobalt (III) nonafluoro-tert-butoxide,
N,N'-bis(3-tert-butyl-5-triphenylmethylsalicylidene)-1,2-cyclohexanediamino cobalt (III) 4-phenoxyphenolate,
N,N'-bis[5-tert-butyl-3-(1-methyl-1-phenylethyl)salicylidene]-1,2-cyclohexanediamino cobalt (III) acetate,
N,N'-bis[5-tert-butyl-3-(1-methyl-1-phenylethyl)salicylidene]-1,2-cyclohexanediamino cobalt (III) nonafluoro-tert-butoxide,
N,N'-bis[5-tert-butyl-3-(1-methyl-1-phenylethyl)salicylidene]-1,2-cyclohexanediamino cobalt (III) 4-phenoxyphenolate,
N,N'-bis(3,5-di-tert-butylsalicylidene)-1,2-diphenylethylenediamino cobalt (III) acetate,
N,N'-bis(3,5-di-tert-butylsalicylidene)-1,2-diphenylethylenediamino cobalt (III) nonafluoro-tert-butoxide,
N,N'-bis(3,5-di-tert-butylsalicylidene)-1,2-diphenylethylenediamino cobalt (III) hexafluoroisopropoxide,
N,N'-bis(3,5-di-tert-butylsalicylidene)-1,2-diphenylethylenediamino cobalt (III) 4-phenoxyphenolate,
N,N'-bis(3,5-di-tert-pentylsalicylidene)-1,2-diphenylethylenediamino cobalt (III) acetate,
N,N'-bis(3,5-di-tert-pentylsalicylidene)-1,2-diphenylethylenediamino cobalt (III) 4-phenoxyphenolate,
N,N'-bis(3,5-di-tert-butylsalicylidene)-1,1'-binaphthalene-2,2'-diamino cobalt (III) acetate,
N,N'-bis(3,5-di-tert-butylsalicylidene)-1,1'-binaphthalene-2,2'-diamino cobalt (III) 4-phenoxyphenolate,
N,N'-bis(3,5-di-tert-butylsalicylidene)-1,2-cyclohexanediamino chromium (III) acetate,
N,N'-bis(3,5-di-tert-butylsalicylidene)-1,2-cyclohexanediamino chromium (III) nonafluoro-tert-butoxide,
N,N'-bis(3,5-di-tert-butylsalicylidene)-1,2-cyclohexanediamino chromium (III) 4-phenoxyphenolate,
N,N'-bis(salicylidene)-1,2-cyclohexanediamino chromium (III) acetate,
N,N'-bis(salicylidene)-1,2-cyclohexanediamino chromium (III) nonafluoro-tert-butoxide,
N,N'-bis(salicylidene)-1,2-cyclohexanediamino chromium (III) 4-phenoxyphenolate,
N,N'-bis(3-tert-butyl-5-methylsalicylidene)-1,2-cyclohexanediamino chromium (III) acetate,
N,N'-bis(3-tert-butyl-5-methylsalicylidene)-1,2-cyclohexanediamino chromium (III) 4-phenoxyphenolate,
N,N'-bis(3-tert-butyl-5-nitrosalicylidene)-1,2-cyclohexanediamino chromium (III) acetate, N,N'-bis(3-tert-butyl-5-nitrosalicylidene)-1,2-cyclohexanediamino chromium (III) 4-phenoxyphenolate,
N,N'-bis(3-tert-butyl-5-methoxysalicylidene)-1,2-cyclohexanediamino chromium (III) acetate,
N,N'-bis(3-tert-butyl-5-methoxysalicylidene)-1,2-cyclohexanediamino chromium (III) 4-phenoxyphenolate,
N,N'-bis(3-tert-butyl-5-chlorosalicylidene)-1,2-cyclohexanediamino chromium (III) acetate,
N,N'-bis(3-tert-butyl-5-chlorosalicylidene)-1,2-cyclohexanediamino chromium (III) 4-phenoxyphenolate,
N,N'-bis(3-tert-butylsalicylidene)-1,2-cyclohexanediamino chromium (III) acetate,
N,N'-bis(3-tert-butylsalicylidene)-1,2-cyclohexanediamino chromium (III) 4-phenoxyphenolate,
N,N'-bis(3,5-di-tert-butylsalicylidene)-1,2-diphenylethylenediamino chromium (III) acetate,
N,N'-bis(3,5-di-tert-butylsalicylidene)-1,2-diphenylethylenediamino chromium (III) nonafluoro-tert-butoxide,
N,N'-bis(3,5-di-tert-butylsalicylidene)-1,2-diphenylethylenediamino chromium (III) 4-phenoxyphenolate,
N,N'-bis(3,5-di-tert-butylsalicylidene)-1,1'-binaphthalene-2,2'-diamino chromium (III) acetate,
N,N'-bis(3,5-di-tert-butylsalicylidene)-1,1'-binaphthalene-2,2'-diamino chromium (III) 4-phenoxyphenolate,
N,N'-bis(3,5-di-tert-butylsalicylidene)-1,2-cyclohexanediamino manganese (III) acetate,
N,N'-bis(3,5-di-tert-butylsalicylidene)-1,2-cyclohexanediamino manganese (III) nonafluoro-tert-butoxide,
N,N'-bis(3,5-di-tert-butylsalicylidene)-1,2-cyclohexanediamino manganese (III) 4-phenoxyphenolate,
N,N'-bis(salicylidene)-1,2-cyclohexanediamino manganese (III) acetate,
N,N'-bis(salicylidene)-1,2-cyclohexanediamino manganese (III) 4-phenoxyphenolate,
N,N'-bis(3-tert-butyl-5-methylsalicylidene)-1,2-cyclohexanediamino manganese (III) acetate,
N,N'-bis(3-tert-butyl-5-methylsalicylidene)-1,2-cyclohexanediamino manganese (III) nonafluoro-tert-butoxide,
N,N'-bis(3-tert-butyl-5-nitrosalicylidene)-1,2-cyclohexanediamino manganese (III) acetate,
N,N'-bis(3-tert-butyl-5-nitrosalicylidene)-1,2-cyclohexanediamino manganese (III) 4-phenoxyphenolate,
N,N'-bis(3-tert-butyl-5-methoxysalicylidene)-1,2-cyclohexanediamino manganese (III) acetate,
N,N'-bis(3-tert-butyl-5-methoxysalicylidene)-1,2-cyclohexanediamino manganese (III) 4-phenoxyphenolate,
N,N'-bis(3-tert-butyl-5-chlorosalicylidene)-1,2-cyclohexanediamino manganese (III) acetate,
N,N'-bis(3-tert-butyl-5-chlorosalicylidene)-1,2-cyclohexanediamino manganese (III) 4-phenoxyphenolate,
N,N'-bis(3-tert-butylsalicylidene)-1,2-cyclohexanediamino manganese (III) acetate,
N,N'-bis(3-tert-butylsalicylidene)-1,2-cyclohexanediamino manganese (III) 4-phenoxyphenolate,
N,N'-bis[5-methyl-3-(1-methyl-1-phenylethyl)salicylidene]-1,2-cyclohexanediamino manganese (III) acetate,
N,N'-bis[5-methyl-3-(1-methyl-1-phenylethyl)salicylidene]-1,2-cyclohexanediamino manganese (III) 4-phenoxyphenolate,
N,N'-bis(3-tert-butyl-5-triphenylmethylsalicylidene)-1,2-cyclohexanediamino manganese (III) acetate,
N,N'-bis(3-tert-butyl-5-triphenylmethylsalicylidene)-1,2-cyclohexanediamino manganese (III) 4-phenoxyphenolate,
N,N'-bis[5-tert-butyl-3-(1-methyl-1-phenylethyl)salicylidene]-1,2-cyclohexanediamino manganese (III) acetate,
N,N'-bis[5-tert-butyl-3-(1-methyl-1-phenylethyl)salicylidene]-1,2-cyclohexanediamino manganese (III) 4-phenoxyphenolate,
N,N'-bis(3,5-di-tert-butylsalicylidene)-1,2-diphenylethylenediamino manganese (III) acetate,
N,N'-bis(3,5-di-tert-butylsalicylidene)-1,2-diphenylethylenediamino manganese (III) nonafluoro-tert-butoxide,
N,N'-bis(3,5-di-tert-butylsalicylidene)-1,2-diphenylethylenediamino manganese (III) 4-phenoxyphenolate,
N,N'-bis(3,5-di-tert-butylsalicylidene)-1,1'-binaphthalene-2,2'-diamino manganese (III) acetate, and
N,N'-bis(3,5-di-tert-butylsalicylidene)-1,1'-binaphthalene-2,2'-diamino manganese (III) 4-phenoxyphenolate.

The optically active metal complexes of formula (1') or (1'a) may include:
(R,R)-(−)-N,N'-bis(3,5-di-tert-butylsalicylidene)-1,2-cyclohexanediamino cobalt (III) acetate,
(R,R)-(−)-N,N'-bis(3,5-di-tert-butylsalicylidene)-1,2-cyclohexanediamino cobalt (III) nonafluoro-tert-butoxide,
(R,R)-(−)-N,N'-bis(3,5-di-tert-butylsalicylidene)-1,2-cyclohexanediamino cobalt (III) hexafluoroisopropoxide,
(R,R)-(−)-N,N'-bis(3,5-di-tert-butylsalicylidene)-1,2-cyclohexanediamino cobalt (III) 4-phenoxyphenolate,
(R,R)-(−)-N,N'-bis(salicylidene)-1,2-cyclohexanediamino cobalt (III) acetate,
(R,R)-(−)-N,N'-bis(salicylidene)-1,2-cyclohexanediamino cobalt (III) nonafluoro-tert-butoxide,
(R,R)-(−)-N,N'-bis(salicylidene)-1,2-cyclohexanediamino cobalt (III) 4-phenoxyphenolate,
(R,R)-(−)-N,N'-bis(3-tert-butyl-5-methylsalicylidene)-1,2-cyclohexanediamino cobalt (III) acetate
(R,R)-(−)-N,N'-bis(3-tert-butyl-5-methylsalicylidene)-1,2-cyclohexanediamino cobalt (III) nonafluoro-tert-butoxide,
(R,R)-(−)-N,N'-bis(3-tert-butyl-5-methylsalicylidene)-1,2-cyclohexanediamino cobalt (III) 4-phenoxyphenolate,
(R,R)-(−)-N,N'-bis(3-tert-butyl-5-nitrosalicylidene)-1,2-cyclohexanediamino cobalt (III) acetate,
(R,R)-(−)-N,N'-bis(3-tert-butyl-5-nitrosalicylidene)-1,2-cyclohexanediamino cobalt (III) nonafluoro-tert-butoxide,
(R,R)-(−)-N,N'-bis(3-tert-butyl-5-nitrosalicylidene)-1,2-cyclohexanediamino cobalt (III) 4-phenoxyphenolate,
(R,R)-(−)-N,N'-bis(3-tert-butyl-5-methoxysalicylidene)-1,2-cyclohexanediamino cobalt (III) acetate,
(R,R)-(−)-N,N'-bis(3-tert-butyl-5-methoxysalicylidene)-1,2-cyclohexanediamino cobalt (III) nonafluoro-tert-butoxide,
(R,R)-(−)-N,N'-bis(3-tert-butyl-5-methoxysalicylidene)-1,2-cyclohexanediamino cobalt (III) 4-phenoxyphenolate,
(R,R)-(−)-N,N'-bis(3-tert-butyl-5-chlorosalicylidene)-1,2-cyclohexanediamino cobalt (III) acetate,
(R,R)-(−)-N,N'-bis(3-tert-butyl-5-chlorosalicylidene)-1,2-cyclohexanediamino cobalt (III) nonafluoro-tert-butoxide,
(R,R)-(−)-N,N'-bis(3-tert-butyl-5-chlorosalicylidene)-1,2-cyclohexanediamino cobalt (III) 4-phenoxyphenolate,
(R,R)-(−)-N,N'-bis(3-tert-butylsalicylidene)-1,2-cyclohexanediamino cobalt (III) acetate,
(R,R)-(−)-N,N'-bis(3-tert-butylsalicylidene)-1,2-cyclohexanediamino cobalt (III) nonafluoro-tert-butoxide,
(R,R)-(−)-N,N'-bis(3-tert-butylsalicylidene)-1,2-cyclohexanediamino cobalt (III) 4-phenoxyphenolate, (R,R)-(−)-N,N'-bis[(5-methyl-3-(1-methyl-1-phenylethyl) salicylidene)-1,2-cyclohexanediamino cobalt (III) acetate, (R,R)-(−)-N,N'-bis[(5-methyl-3-(1-methyl-1-phenylethyl) salicylidene)-1,2-cyclohexanediamino cobalt (III) nonafluoro-tert-butoxide, (R,R)-(−)-N,N'-bis[(5-methyl-3-(1-methyl-1-phenylethyl) salicylidene)-1,2-cyclohexanediamino cobalt (III) 4-phenoxyphenolate, (R,R)-(−)-N,N'-bis(3-tert-butyl-5-triphenylmethylsalicylidene)-1,2-cyclohexanediamino cobalt (III) acetate, (R,R)-(−)-N,N'-bis(3-tert-butyl-5-triphenylmethylsalicylidene)-1,2-cyclohexanediamino cobalt (III) nonafluoro-tert-butoxide, (R,R)-(−)-N,N'-bis(3-tert-butyl-5-triphenylmethylsalicylidene)-1,2-cyclohexanediamino cobalt (III) 4-phenoxyphenolate, (R,R)-(−)-N,N'-bis[5-tert-butyl-3-(1-methyl-1-phenylethyl) salicylidene]-1,2-cyclohexanediamino cobalt (III) acetate, (R,R)-(−)-N,N'-bis[5-tert-butyl-3-(1-methyl-1-phenylethyl) salicylidene]-1,2-cyclohexanediamino cobalt (III) nonafluoro-tert-butoxide, (R,R)-(−)-N,N'-bis[5-tert-butyl-3-(1-methyl-1-phenylethyl) salicylidene]-1,2-cyclohexanediamino cobalt (III) 4-phenoxyphenolate, (R,R)-(−)-N,N'-bis(3,5-di-tert-butylsalicylidene)-1,2-diphenylethylenediamino cobalt (III) acetate, (R,R)-(−)-N,N'-bis(3,5-di-tert-butylsalicylidene)-1,2-diphenylethylenediamino cobalt (III) nonafluoro-tert-butoxide, (R,R)-(−)-N,N'-bis(3,5-di-tert-butylsalicylidene)-1,2-diphenylethylenediamino cobalt (III) hexafluoroisopropoxide, (R,R)-(−)-N,N'-bis(3,5-di-tert-butylsalicylidene)-1,2-diphenylethylenediamino cobalt (III) 4-phenoxyphenolate, (R)-(+)-N,N'-bis(3,5-di-tert-butylsalicylidene)-1,1'-binaphthalene-2,2'-diamino cobalt (III) acetate, (R)-(+)-N,N'-bis(3,5-di-tert-butylsalicylidene)-1,1'-binaphthalene-2,2'-diamino cobalt (III) 4-phenoxyphenolate, (R,R)-(−)-N,N'-bis(3,5-di-tert-butylsalicylidene)-1,2-cyclohexanediamino chromium (III) acetate, (R,R)-(−)-N,N'-bis(3,5-di-tert-butylsalicylidene)-1,2-cyclohexanediamino chromium (III) nonafluoro-tert-butoxide, (R,R)-(−)-N,N'-bis(3,5-di-tert-butylsalicylidene)-1,2-cyclohexanediamino chromium (III) 4-phenoxyphenolate, (R,R)-(−)-N,N'-bis(salicylidene)-1,2-cyclohexanediamino chromium (III) acetate, (R,R)-(−)-N,N'-bis(salicylidene)-1,2-cyclohexanediamino chromium (III) nonafluoro-tert-butoxide, (R,R)-(−)-N,N'-bis(salicylidene)-1,2-cyclohexanediamino chromium (III) 4-phenoxyphenolate, (R,R)-(−)-N,N'-bis(3-tert-butyl-5-methylsalicylidene)-1,2-cyclohexanediamino chromium (III) acetate, (R,R)-(−)-N,N'-bis(3-tert-butyl-5-methylsalicylidene)-1,2-cyclohexanediamino chromium (III) 4-phenoxyphenolate, (R,R)-(−)-N,N'-bis(3-tert-butyl-5-nitrosalicylidene)-1,2-cyclohexanediamino chromium (III) acetate, (R,R)-(−)-N,N'-bis(3-tert-butyl-5-nitrosalicylidene)-1,2-cyclohexanediamino chromium (III) 4-phenoxyphenolate, (R,R)-(−)-N,N'-bis(3-tert-butyl-5-methoxysalicylidene)-1,2-cyclohexanediamino chromium (III) acetate, (R,R)-(−)-N,N'-bis(3-tert-butyl-5-methoxysalicylidene)-1,2-cyclohexanediamino chromium (III) 4-phenoxyphenolate, (R,R)-(−)-N,N'-bis(3-tert-butyl-5-chlorosalicylidene)-1,2-cyclohexanediamino chromium (III) acetate, (R,R)-(−)-N,N'-bis(3-tert-butyl-5-chlorosalicylidene)-1,2-cyclohexanediamino chromium (III) 4-phenoxyphenolate, (R,R)-(−)-N,N'-bis(3-tert-butylsalicylidene)-1,2-cyclohexanediamino chromium (III) acetate, (R,R)-(−)-N,N'-bis(3-tert-butylsalicylidene)-1,2-cyclohexanediamino chromium (III) 4-phenoxyphenolate, (R,R)-(−)-N,N'-bis(3,5-di-tert-butylsalicylidene)-1,2-diphenylethylenediamino chromium (III) acetate, (R,R)-(−)-N,N'-bis(3,5-di-tert-butylsalicylidene)-1,2-diphenylethylenediamino chromium (III) nonafluoro-tert-butoxide, (R,R)-(−)-N,N'-bis(3,5-di-tert-butylsalicylidene)-1,2-diphenylethylenediamino chromium (III) 4-phenoxyphenolate, (R)-(+)-N,N'-bis(3,5-di-tert-butylsalicylidene)-1,1'-binaphthalene-2,2'-diamino chromium (III) acetate, (R)-(+)-N,N'-bis(3,5-di-tert-butylsalicylidene)-1,1'-binaphthalene-2,2'-diamino chromium (III) 4-phenoxyphenolate, (R,R)-(−)-N,N'-bis(3,5-di-tert-butylsalicylidene)-1,2-cyclohexanediamino manganese (III) acetate, (R,R)-(−)-N,N'-bis(3,5-di-tert-butylsalicylidene)-1,2-cyclohexanediamino manganese (III) nonafluoro-tert-butoxide, (R,R)-(−)-N,N'-bis(3,5-di-tert-butylsalicylidene)-1,2-cyclohexanediamino manganese (III) 4-phenoxyphenolate, (R,R)-(−)-N,N'-bis(salicylidene)-1,2-cyclohexanediamino manganese (III) acetate, (R,R)-(−)-N,N'-bis(salicylidene)-1,2-cyclohexanediamino manganese (III) 4-phenoxyphenolate, (R,R)-(−)-N,N'-bis(3-tert-butyl-5-methylsalicylidene)-1,2-cyclohexanediamino manganese (III) acetate, (R,R)-(−)-N,N'-bis(3-tert-butyl-5-methylsalicylidene)-1,2-cyclohexanediamino manganese (III) nonafluoro-tert-butoxide, (R,R)-(−)-N,N'-bis(3-tert-butyl-5-nitrosalicylidene)-1,2-cyclohexanediamino manganese (III) acetate, (R,R)-(−)-N,N'-bis(3-tert-butyl-5-nitrosalicylidene)-1,2-cyclohexanediamino manganese (III) 4-phenoxyphenolate, (R,R)-(−)-N,N'-bis(3-tert-butyl-5-methoxysalicylidene)-1,2-cyclohexanediamino manganese (III) acetate, (R,R)-(−)-N,N'-bis(3-tert-butyl-5-methoxysalicylidene)-1,2-cyclohexanediamino manganese (III) 4-phenoxyphenolate, (R,R)-(−)-N,N'-bis(3-tert-butyl-5-chlorosalicylidene)-1,2-cyclohexanediamino manganese (III) acetate, (R,R)-(−)-N,N'-bis(3-tert-butyl-5-chlorosalicylidene)-1,2-cyclohexanediamino manganese (III) 4-phenoxyphenolate, (R,R)-(−)-N,N'-bis(3-tert-butylsalicylidene)-1,2-cyclohexanediamino manganese (III) acetate, (R,R)-(−)-N,N'-bis(3-tert-butylsalicylidene)-1,2-cyclohexanediamino manganese (III) 4-phenoxyphenolate, (R,R)-(−)-N,N'-bis[5-methyl-3-(1-methyl-1-phenylethyl) salicylidene]-1,2-cyclohexanediamino manganese (III) acetate, (R,R)-(−)-N,N'-bis[5-methyl-3-(1-methyl-1-phenylethyl) salicylidene]-1,2-cyclohexanediamino manganese (III) 4-phenoxyphenolate, (R,R)-(−)-N,N'-bis(3-tert-butyl-5-triphenylmethylsalicylidene)-1,2-cyclohexanediamino manganese (III) acetate, (R,R)-(−)-N,N'-bis(3-tert-butyl-5-triphenylmethylsalicylidene)-1,2-cyclohexanediamino manganese (III) 4-phenoxyphenolate, (R,R)-(−)-N,N'-bis[5-tert-butyl-3-(1-methyl-1-phenylethyl) salicylidene]-1,2-cyclohexanediamino manganese (III) acetate, (R,R)-(−)-N,N'-bis[5-tert-butyl-3-(1-methyl-1-phenylethyl) salicylidene]-1,2-cyclohexanediamino manganese (III) 4-phenoxyphenolate, (R,R)-(−)-N,N'-bis(3,5-di-tert-butylsalicylidene)-1,2-diphenylethylenediamino manganese (III) acetate, (R,R)-(−)-N,N'-bis(3,5-di-tert-butylsalicylidene)-1,2-diphenylethylenediamino manganese (III) nonafluoro-tert-butoxide, (R,R)-(−)-N,N'-bis(3,5-di-tert-butylsalicylidene)-1,2-diphenylethylenediamino manganese (III) 4-phenoxyphenolate, (R)-(+)-N,N'-bis(3,5-di-tert-butylsalicylidene)-1,1'-binaphthalene-2,2'-diamino manganese (III) acetate, (R)-(+)-N,N'-bis(3,5-di-tert-butylsalicylidene)-1,1'-binaphthalene-2,2'-diamino manganese (III) 4-phenoxyphenolate, and similar optically active metal complexes in which the above configuration (R,R)-(−) or (R)-(+) is changed to (S,S)-(+) or (S)-(−), respectively.

The Lewis acid may include aluminum halides, dialkyl aluminum halides, trialkoxy aluminum, titanium halides, tetraalkoxy titanium, boron halides and zinc halides.

The aluminum halides may include aluminum chloride and aluminum bromide. The dialkyl aluminum halides may include diethyl aluminum chloride, diethyl aluminum bromide and diisopropyl aluminum chloride. The trialkoxy aluminum may include triethoxy aluminum, triisopropoxy aluminum and tri-tert-butoxy aluminum. The titanium halides may include titanium tetrachloride. The tetraalkoxy titanium may include tetraisopropoxy titanium. The boron halides may include boron trifluoride, boron trichloride and boron tribromide. The zinc halides may include zinc chloride and zinc bromide.

The Lewis acid may be used as such or as a solution in an organic solvent. The Lewis acid, which is unstable to, for example, air or water and which requires careful handling, may preferably be used as a solution in an organic solvent. The organic solvent is not particularly limited, so long as it is inert to the Lewis acid, and may include aliphatic hydrocarbon solvents such as hexane and heptane; and ether solvents such as diethyl ether and tert-butyl methyl ether. Further, complex compounds of Lewis acids such as boron trifluoride-diethyl ether complex compounds may also be used.

The amount of Lewis acid used is not particularly limited, but is usually 0.2 to 5 moles, preferably 0.5 to 2 moles, relative to 1 mole of metal complex (1).

The metal complex catalyst of the present invention can be produced by reacting metal complex (1) with a Lewis acid, and the reaction is usually carried out in an organic solvent by contacting and mixing both of them. When both of them are contacted and mixed, the reaction will occur to form a novel complex. The production of a novel (asymmetric) complex is achieved by, for example, mixing both of them in an organic solvent, which causes the change of color in the reaction mixture, thereby making it possible to verify that the metal complex is being reacted with the Lewis acid to form a novel (asymmetric) complex. For example, when (−)-N,N'-bis(3,5-di-tert-butylsalicylidene)-1,2-cyclohexanediamino cobalt (III) 4-phenoxyphenolate is mixed with aluminum chloride in tert-butyl methyl ether, the color of the mixture changes from brown to dark green.

The reaction temperature in the reaction of metal complex (1) with a Lewis acid is usually −50 to 50° C., preferably −25 to 40° C.

The organic solvent may include ether solvents such as diethyl ether and tert-butyl methyl ether; aromatic hydrocarbon solvents such as toluene; halogenated hydrocarbon solvents such as chlorobenzene and chloroform; and aliphatic hydrocarbon solvents such as hexane. The amounts for their use are not particularly limited.

If, for example, water is present in the reaction system, Lewis acids are easily decomposed; therefore, the reagents, solvents to be used and the like may preferably be subjected to dehydration in advance or dehydrating agents such as molecular sieves may preferably be allowed to coexist in the reaction system.

When metal complex (1) is reacted with a Lewis acid in an organic solvent, the solution containing a novel complex catalyst produced may be used as such in the reaction of cyclic ether compound (2) with phenol derivative (3), or the novel complex catalyst may be separated before use by, for example, concentration of the above solution.

In this step, the use of a metal complex of formula (1') or (1'a) makes it possible to obtain an asymmetric complex catalyst. The reaction of cyclic ether compound (2) with phenol derivative (3) in the presence of this catalyst makes it possible to the desired optically active alcohol derivative by the reaction exhibiting excellent regio- and stereo-selectivity.

Next, the following will describe the step of reacting a cyclic ether compound with a phenol derivative in the presence of the complex catalyst obtained above to give an alcohol derivative.

The cyclic ether compound may be any reactive cyclic ether compound which causes ring-opening reaction by the reaction with a phenol derivative, and may include cyclic ether compounds of the following formula (2):

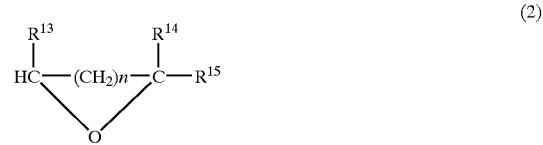

(2)

(hereinafter abbreviated as cyclic ether compound (2))

wherein $R^{13}$ is hydrogen; $R^{14}$ is hydrogen or alkyl; or $R^{13}$ and $R^{14}$ are combined together to represent alkylene of 2 to 6 carbon toms; $R^{15}$ is alkyl, aryl or, aralkyl; wherein the alkyl, aryl or aralkyl group may have a substituent(s); and n is 0 or 1.

When the cyclic ether compound has an asymmetric carbon atom(s) in the molecule, it may be an optically active form or a mixture of the optically active forms.

The alkyl group represented by $R^{14}$ may include alkyl groups of 1 to 4 carbon atoms such as methyl, ethyl, n-propyl, isopropyl, n-butyl and isobutyl. The alkylene group of 2 to 6 carbon atoms formed by combining $R^{13}$ and $R^{14}$ together may include ethylene, propylene, butylene, pentylene and hexylene.

Further, $R^{15}$ represents alkyl, aryl or aralkyl. The alkyl group may include the same as described for $R^{14}$. The aryl group may include phenyl and naphthyl. The aralkyl group may include those composed of such alkyl and aryl groups, and may include benzyl and phenylethyl. These alkyl, aryl and aralkyl groups may have a substituent(s), and the substituent(s) which may include halogen as described above, such as chlorine and fluorine, hydroxyl and alkoxy such as methoxy and ethoxy.

Specific examples of cyclic ether compound (2) may include propylene oxide, 1,2-epoxybutane, 1,2-epoxyhexane, 1,3-epoxyhexane, 1,2-epoxy-4-methylpentane, 1,2-epoxy-3-phenylpropane, styrene oxide, 1-chloro-2,3-epoxypropane, 1-bromo-2,3-epoxypropane, 2,3-epoxy-1-propanol, cyclohexene oxide, cyclopentene oxide and 1,2-epoxycyclooctane.

The preferred cyclic ether compound may include propylene oxide and 1,2-epoxybutane.

The phenol derivative may be any phenol having a phenolic hydroxyl group or any thiophenol derivative obtained by replacing the oxygen atom in the hydroxyl group of the phenol derivative by a sulfur atom, which may include phenol derivatives of formula (3):

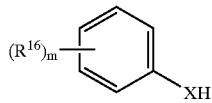

(3)

(hereinafter abbreviated as phenol derivative (3))

wherein X is oxygen or sulfur; $R^{16}$'s are the same or different and are independently hydrogen, halogen, nitro, alkyl of 1 to 6 carbon atoms, alkoxy of 1 to 6 carbon atoms, phenylthio, benzyl or phenoxy; and m is an integer of 0 to 5; wherein the alkyl group of 1 to 6 carbon atoms, the alkoxy group of 1 to 6 carbon atoms, the phenylthio, benzyl or phenoxy group may optionally be substituted with alkyl of 1 to 4 carbon atoms, alkoxy of 1 to 4 carbon atoms, haloalkyl of 1 to 4 carbon atoms, haloalkoxy of 1 to 4 carbon atoms or halogen.

The halogen atom, the alkyl group of 1 to 6 carbon atoms and the alkoxy group of 1 to 6 carbon atoms, which are represented by $R^{16}$, may include the same as described above. The haloalkyl group of 1 to 4 carbon atoms may include chloromethyl and trifluoromethyl. The haloalkoxy group of 1 to 4 carbon atoms may include chloromethoxy.

The phenol derivative may include compounds of the above formula (3) wherein $R^{16}$ is hydrogen, halogen, nitro, alkyl of 1 to 4 carbon atoms, alkoxy of 1 to 4 carbon atoms, or phenoxy; provided that the alkyl group of 1 to 4 carbon atoms, the alkoxy group of 1 to 4 carbon atoms, or the phenoxy group may optionally be substituted with alkyl of 1 to 4 carbon atoms, alkoxy of 1 to 4 carbon atoms, haloalkyl of 1 to 4 carbon atoms, haloalkoxy of 1 to 4 carbon atoms, or halogen; and phenol derivatives of formula (3a):

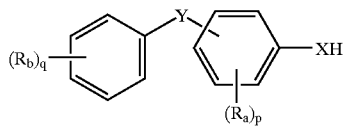

(3a)

wherein X is oxygen or sulfur; Y is oxygen, sulfur or methylene; $R_a$'s are independently halogen or methyl; $R_b$'s are the same or different and are independently hydrogen, halogen, alkyl of 1 to 4 carbon atoms, alkoxy of 1 to 4 carbon atoms, or trifluoromethyl; p is an integer of 0 to 4; and q is an integer of 0 to 2.

The phenol derivative (3) may include phenol, 4-chlorophenol, 2-bromophenol, 4-bromophenol, o-cresol, m-cresol, p-cresol, 4-methoxyphenol, 4-phenoxyphenol, 4-nitrophenol, 2,3-difluoro-6-nitrophenol, thiophenol, 2-bromo-4-methylthiophenol, 4-chlorothiophenol, 4-methoxythiophenol, 4-phenoxythiophenol, 4-(3-methylphenoxy)phenol, 4-(2-fluorophenoxy)phenol, 4-(3-fluorophenoxy)phenol, 4-(4-fluorophenoxy)phenol, 4-(3,5-difluorophenoxy)phenol, 4-(3,5-dichlorophenoxy)phenol, 4-(3-trifluoromethylphenoxy)phenol, 4-(3-methoxyphenoxy)phenol, 4-benzylphenol and 4-phenoxythiophenol.

The preferred phenol derivative (3) may include 4-phenoxyphenol, 4-(3-methylphenoxy)phenol, 4-(2-fluorophenoxy)phenol, 4-(3-fluorophenoxy)phenol, 4-(4-fluorophenoxy)phenol, 4-(3,5-difluorophenoxy)phenol, 4-(3,5-dichlorophenoxy)phenol, 4-(3-trifluoromethylphenoxy)phenol, 4-(3-methoxyphenoxy)phenol, 4-benzylphenol and 4-phenoxythiophenol.

The amount of cyclic ether compound used is usually 1 mole or more (2 moles or more when an asymmetric complex catalyst is used), relative to 1 mole of phenol derivative, and there is no particular upper limit thereof. Since too large amounts may easily result in an economical disadvantage, the amount thereof is practically 5 moles or less (10 moles or less when an asymmetric complex catalyst is used).

The complex catalyst comprising metal complex (1) and a Lewis acid, although it exhibits sufficient activity in a catalytic amount, may exhibit sufficient catalytic activity, preferably in amounts for use ranging from 0.1 to 3 mol %, relative to 1 mole of phenol derivative. Of course, amounts larger than 3 mol % may be used; however, larger amounts for use will easily result in an economical disadvantage. Therefore, practical amounts for use are as described above.

The reaction temperature is usually −50 to 50° C., preferably −25 to 40° C.

The reaction is achieved by contacting or mixing a complex catalyst, which has been obtained by reacting metal complex (1) with a Lewis acid; a cyclic ether compound and a phenol derivative. The order of mixing is not particularly limited.

The reaction is usually carried out in the presence of an organic solvent. The organic solvent may include single or mixed solvents selected from aliphatic hydrocarbon solvents such as hexane and heptane; aromatic hydrocarbon solvents such as toluene; ether solvents such as diethyl ether and tert-butyl methyl ether; and halogenated hydrocarbon solvents such as chloroform and chlorobenzene. The amounts for their use are not particularly limited.

After completion of the reaction, the reaction mixture containing an alcohol derivative may be used as such in the subsequent step or, for example, the reaction mixture may be subjected to concentration to separate the alcohol derivative, which is then used in the subsequent step. Further, for example, water and, if necessary, a water-insoluble organic solvent may be added to the reaction mixture, followed by extraction, providing the organic layer containing the alcohol derivative, which organic layer may be used in the subsequent step or may be subjected to concentration to separate the alcohol derivative, which is then used in the subsequent step. The separated alcohol derivative may be further purified by an ordinary means of purification, such as distillation, recrystallization and column chromatography, and then used in the subsequent step. The water-insoluble organic solvent may include aromatic hydrocarbon solvents such as toluene and xylene; aliphatic hydrocarbon solvents such as hexane and heptane; halogenated hydrocarbon solvents such as chloroform and chlorobenzene; and ether solvents such as diethyl ether and tert-butyl methyl ether. The amounts for their use are not particularly limited.

The above cyclic ether compound (2) is reacted with the above phenol derivative (3) to give an alcohol derivative of formula (4):

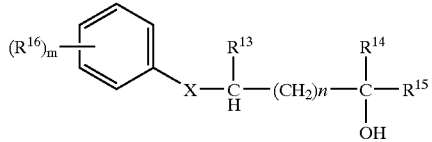

(hereinafter abbreviated as alcohol derivative (4))

wherein $R^{13}$, $R^{14}$, $R^{15}$, $R^{16}$, X, m and n are as defined above.

The above alcohol derivative may include alcohol derivatives of the following formula (4a):

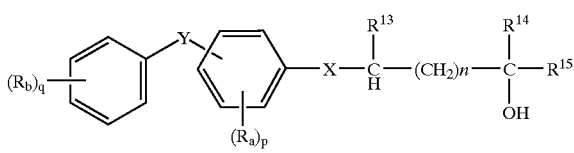

(hereinafter abbreviated as alcohol derivative (4a))

wherein $R^{13}$, $R^{14}$, $R^{15}$, $R_a$, $R_b$, X, Y, n, p and q are as defined above.

The alcohol derivatives (4) and (4a) thus obtained may include:
1-phenoxy-2-propanol,
1-(4-chlorophenoxy)-2-propanol,
1-(2-bromophenoxy)-2-propanol,
1-(4-bromophenoxy)-2-propanol,
1-(2-methylphenoxy)-2-propanol,
1-(3-methylphenoxy)-2-prop anol,
1-(4-methylphenoxy)-2-propanol,
1-(4-methoxyphenoxy)-2-propanol,
1-(4-phenoxyphenoxy)-2-propanol,
1-(4-nitrophenoxy)-2-propanol,
1-(2,3-difluoro-6-nitrophenoxy)-2-propanol,
1-phenylthio-2-propanol,
1-(2-bromo-4-methylphenylthio)-2-propanol,
1-(4-chlorophenylthio)-2-propanol,
1-(4-methoxyphenylthio)-2-propanol,
1-(4-phenoxyphenylthio)-2-propanol,
1-phenoxy-2-butanol,
1-(4-chlorophenoxy)-2-butanol,
1-(2-bromophenoxy)-2-butanol,
1-(4-bromophenoxy)-2-butanol,
1-(2-methylphenoxy)-2-butanol,
1-(3-methylphenoxy)-2-butanol,
1-(4-methylphenoxy)-2-butanol,
1-(4-methoxyphenoxy)-2-butanol,
1-(4-phenoxyphenoxy)-2-butanol,
1-(4-nitrophenoxy)-2-butanol,
1-(2,3-difluoro-6-nitrophenoxy)-2-butanol,
1-phenylthio-2-butanol,
1-(2-bromo-4-methylphenylthio)-2-butanol,
1-(4-chlorophenylthio)-2-butanol,
1-(4-methoxyphenylthio)-2-butanol,
1-(4-phenoxyphenylthio)-2-butanol,
1-phenoxy-2-hexanol,
1-(4-chlorophenoxy)-2-hexanol,
1-(2-bromophenoxy)-2-hexanol,
1-(4-bromophenoxy)-2-hexanol,
1-(2-methylphenoxy)-2-hexanol,
1-(3-methylphenoxy)-2-hexanol,
1-(4-methylphenoxy)-2-hexanol,
1-(4-methoxyphenoxy)-2-hexanol,
1-(4-phenoxyphenoxy)-2-hexanol,
1-(4-nitrophenoxy)-2-hexanol,
1-(2,3-difluoro-6-nitrophenoxy)-2-hexanol,
1-phenylthio-2-hexanol,
1-(2-bromo-4-methylphenylthio)-2-hexanol,
1-(4-chlorophenylthio)-2-hexanol,
1-(4-methoxyphenylthio)-2-hexanol,
1-(4-phenoxyphenylthio)-2-hexanol,
2-phenoxy-1-phenylethanol,
2-(4-chlorophenoxy)-1-phenylethanol,
2-(2-bromophenoxy)-1-phenylethanol,
2-(4-bromophenoxy)-1-phenylethanol,
2-(2-methylphenoxy)-1-phenylethanol,
2-(3-methylphenoxy)-1-phenylethanol,
2-(4-methylphenoxy)-1-phenylethanol,
2-(4-methoxyphenoxy)-1-phenylethanol,
2-(4-phenoxyphenoxy)-1-phenylethanol,
2-(4-nitrophenoxy)-1-phenylethanol,
2-(2,3-difluoro-6-nitrophenoxy)-1-phenylethanol,
2-phenylthio-1-phenylethanol,
2-(2-bromo-4-methylphenylthio)-1-phenylethanol,
2-(4-chlorophenylthio)-1-phenylethanol,
2-(4-methoxyphenylthio)-1-phenylethanol,
2-(4-phenoxyphenylthio)-1-phenylethanol,
3-phenoxy-1-chloro-2-propanol,
3-(4-chlorophenoxy)-1-chloro-2-propanol,
3-(2-bromophenoxy)-1-chloro-2-propanol,
3-(4-bromophenoxy)-1-chloro-2-propanol,
3-(2-methylphenoxy)-1-chloro-2-propanol,
3-(3-methylphenoxy)-1-chloro-2-propanol,
3-(4-methylphenoxy)-1-chloro-2-propanol,
3-(4-methoxyphenoxy)-1-chloro-2-propanol,
3-(4-phenoxyphenoxy)-1-chloro-2-propanol,
3-(4-nitrophenoxy)-1-chloro-2-propanol,
3-(2,3-difluoro-6-nitrophenoxy)-1-chloro-2-propanol,
3-phenylthio-1-chloro-2-propanol,
3-(2-bromo-4-methylphenylthio)-1-chloro-2-propanol,
3-(4-chlorophenylthio)-1-chloro-2-propanol,
3-(4-methoxyphenylthio)-1-chloro-2-propanol,
3-(4-phenoxyphenylthio)-1-chloro-2-propanol,
3-phenoxy-1-bromo-2-propanol,
3-(4-chlorophenoxy)-1-bromo-2-propanol,
3-(2-bromophenoxy)-1-bromo-2-propanol,
3-(4-bromophenoxy)-1-bromo-2-propanol,
3-(2-methylphenoxy)-1-bromo-2-propanol,
3-(3-methylphenoxy)-1-bromo-2-propanol,
3-(4-methylphenoxy)-1-bromo-2-propanol,
3-(4-methoxyphenoxy)-1-bromo-2-propanol,
3-(4-phenoxyphenoxy)-1-bromo-2-propanol,
3-(4-nitrophenoxy)-1-bromo-2-propanol,
3-(2,3-difluoro-6-nitrophenoxy)-1-bromo-2-propanol,
3-phenylthio-1-bromo-2-propanol,
3-(2-bromo-4-methylphenylthio)-1-bromo-2-propanol,
3-(4-chlorophenylthio)-1-bromo-2-propanol,
3-(4-methoxyphenylthio)-1-bromo-2-propanol,
3-(4-phenoxyphenylthio)-1-bromo-2-propanol,
3-phenoxy-1,2-propanediol,
3-(4-chlorophenoxy)-1,2-propanediol,
3-(2-bromophenoxy)-1,2-propanediol,
3-(4-bromophenoxy)-1,2-propanediol, 3-(2-methylphenoxy)-1,2-propanediol,
3-(3-methylphenoxy)-1,2-propanediol,
3-(4-methylphenoxy)-1,2-propanediol,
3-(4-methoxyphenoxy)-1,2-propanediol,
3-(4-phenoxyphenoxy)-1,2-propanediol,
3-(4-nitrophenoxy)-1,2-propanediol,
3-(2,3-difluoro-6-nitrophenoxy)-1,2-propanediol,
3-phenylthio-1,2-propanediol,
3-(2-bromo-4-methylphenylthio)-1,2-propanediol,
3-(4-chlorophenylthio)-1,2-propanediol,
3-(4-methoxyphenylthio)-1,2-propanediol,
3-(4-pheoxyphenylthio)-1,2-propanediol,
2-phenoxycyclohexanol,
2-(4-chlorophenoxy)cyclohexanol,
2-(2-bromophenoxy)cyclohexanol,
2-(4-bromophenoxy)cyclohexanol,
2-(2-methylphenoxy)cyclohexanol,
2-(3-methylphenoxy)cyclohexanol,
2-(4-methylphenoxy)cyclohexanol,
2-(4-methoxyphenoxy)cyclohexanol,
2-(4-phenoxyphenoxy)cyclohexanol,
2-(4-nitrophenoxy)cyclohexanol,
2-(2,3-difluoro-6-nitrophenoxy)cyclohexanol,
2-(phenylthio)cyclohexanol,
2-(2-bromo-4-methylphenylthio)cyclohexanol,
2-(4-chlorophenylthio)cyclohexanol,
2-(4-methoxyphenylthio)cyclohexanol,
2-(4-phenoxyphenylthio)cyclohexanol,
2-phenoxycyclopentanol,
2-(4-chlorophenoxy)cyclopentanol,
2-(2-bromophenoxy)cyclopentanol,
2-(4-bromophenoxy)cyclopentanol,
2-(2-methylphenoxy)cyclopentanol,
2-(3-methylphenoxy)cyclopentanol,
2-(4-methylphenoxy)cyclopentanol,
2-(4-methoxyphenoxy)cyclopentanol,
2-(4-phenoxyphenoxy)cyclopentanol,
2-(4-nitrophenoxy)cyclopentanol,
2-(2,3-difluoro-6-nitrophenoxy)cyclopentanol,
2-(phenylthio)cyclopentanol,
2-(2-bromo-4-methylphenylthio)cyclopentanol,
2-(4-chlorophenylthio)cyclopentanol,
2-(4-methoxyphenylthio)cyclopentanol,
2-(4-phenoxyphenylthio)cyclopentanol,
2-phenoxycyclooctanol,
2-(4-chlorophenoxy)cyclooctanol,
2-(2-bromophenoxy)cyclooctanol,
2-(4-bromophenoxy)cyclooctanol,
2-(2-methylphenoxy)cyclooctanol,
2-(3-methylphenoxy)cyclooctanol,
2-(4-methylphenoxy)cyclooctanol,
2-(4-methoxyphenoxy)cyclooctanol,
2-(4-phenoxyphenoxy)cyclooctanol,
2-(4-nitrophenoxy)cyclooctanol,
2-(2,3-difluoro-6-nitrophenoxy)cyclooctanol,
2-(phenylthio)cyclooctanol,
2-(2-bromo-4-methylphenylthio)cyclooctanol,
2-(4-chlorophenylthio)cyclooctanol,
2-(4-methoxyphenylthio)cyclooctanol, and
2-(4-phenoxyphenylthio)cyclooctanol.

The amount of a regio-isomer of the following formula (7):

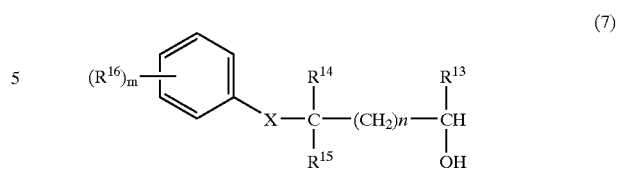

produced as a by-product, which regio-isomer is a by-product in this step, is very small.

The process of reacting the above cyclic ether compound (2) with the above phenol derivative (3) in the presence of an asymmetric complex catalyst makes it possible to obtain an optically active alcohol derivative of formula (4'):

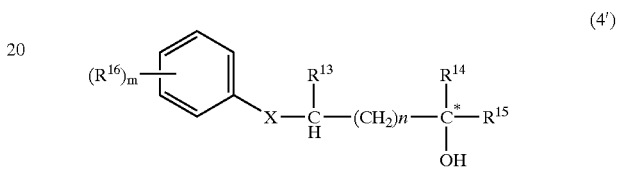

(hereinafter abbreviated as optically active alcohol derivative (4')) wherein $R^{13}$, $R^{14}$, $R^{15}$, $R^{16}$, X, m and n are as defined above and * indicates an asymmetric carbon atom.

The above alcohol derivative may include alcohol derivatives of the following formula (4'a):

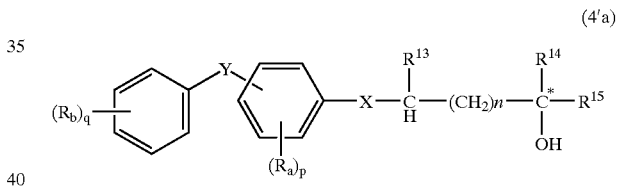

(hereinafter abbreviated as alcohol derivative (4'a)) wherein $R^{13}$, $R^{14}$, $R^{15}$, $R_a$, $R_b$, X, Y, n, p and q are as defined above and * indicates an asymmetric carbon atom.

The optically active alcohol derivatives (4') and (4'a) thus obtained may include:
optically active 1-(4-phenoxyphenoxy)-2-propanol,
optically active 1-[4-(3-methylphenoxy)phenoxy]-2-propanol,
optically active 1-[4-(2-fluorophenoxy)phenoxy]-2-propanol,
optically active 1-[4-(3-fluorophenoxy)phenoxy]-2-propanol,
optically active 1-[4-(4-fluorophenoxy)phenoxy]-2-propanol,
optically active 1-[4-(3,5-difluorophenoxy)phenoxy]-2-propanol,
optically active 1-[4-(3,5-dichlorophenoxy)phenoxy]-2-propanol,
optically active 1-[4-(3-trifluoromethylphenoxy)]-2-propanol,
optically active 1-[4-(3-methoxyphenoxy)phenoxy]-2-propanol,
optically active 1-(4-benzylphenoxy)-2-propanol,
optically active 1-(4-phenylthiophenoxy)-2-propanol,
optically active 1-(4-phenoxyphenoxy)-2-butanol, optically active 1-[4-(3-methylphenoxy)phenoxy]-2-butanol,
optically active 1-[4-(2-fluorophenoxy)phenoxy]-2-butanol,
optically active 1-[4-(3-fluorophenoxy)phenoxy]-2-butanol,
optically active 1-[4-(4-fluorophenoxy)phenoxy]-2-butanol,
optically active 1-[4-(3,5-difluorophenoxy)phenoxy]-2-butanol,
optically active 1-[4-(3,5-dichlorophenoxy)phenoxy]-2-butanol,
optically active 1-[4-(3-trifluoromethylphenoxy)]-2-butanol,
optically active 1-[4-(3-methoxyphenoxy)phenoxy]-2-butanol,
optically active 1-(4-benzylphenoxy)-2-butanol, and optically active 1-(4-phenylthiophenoxy)-2-butanol.

Next, the following will describe the step of reacting the alcohol derivative obtained above with a halogenated nitrogen-containing heterocyclic compound in the presence of a base to give a nitrogen-containing heterocyclic compound. In this step, an optically active alcohol derivative can be reacted with a halogenated nitrogen-containing heterocyclic compound in the presence of a base to give an optically active nitrogen-containing heterocyclic compound.

The halogenated nitrogen-containing heterocyclic compound may be any nitrogen-containing heterocyclic compound having a halogen atom which can be reacted with the hydroxyl group of the above alcohol derivative, and may include halogenated nitrogen-containing heterocyclic compounds of the formula (5):

$$Z\text{-}R^{17} \quad (5)$$

(hereinafter abbreviated as halogenated nitrogen-containing heterocyclic compound (5))

wherein Z is halogen and $R^{17}$ is pyridyl, pyridazinyl, pyrimidinyl, pyrazinyl, triazinyl, 2-thiazolyl or dihydro-2-thiazolyl; wherein these groups may optionally have one or more than one substituent selected from the group consisting of halogen, alkyl of 1 to 4 carbon atoms, alkoxy of 1 to 4 carbon atoms, alkylthio of 1 to 4 carbon atoms, trifluoromethyl or nitro.

The halogen atom, the alkyl group of 1 to 4 carbon atoms and the alkoxy group of 1 to 4 carbon atoms may include the same as described above. The alkylthio group of 1 to 4 carbon atoms may include methylthio, ethylthio, n-propylthio, isopropylthio, n-butylthio, isobutylthio, sec-butylthio and tert-butylthio.

The pyridyl group may include 2-pyridyl, 3-pyridyl and 4-pyridyl. The pyridazinyl group may include 3-pyridazinyl. The pyrimidinyl group may include 2-pyrimidinyl and 4-pyrimidinyl. The pyrazinyl group may include 2-pyrazinyl. The triazinyl group may include 1,3,5-triazin-2-yl.

The halogenated nitrogen-containing heterocyclic compound (5) may include:
2-fluoropyridine, 2-chloropyridine, 2-bromopyridine,
3-chloropyridine, 4-chloropyridine, 2-chloro-5-methylpyridine,
2-chloro-6-methylpyridine, 2-chloro-5-nitropyridine,
2,5-dichloropyridine, 2-chloro-3-nitropyridine,
2,3-dichloro-5-trifluoromethylpyridine,
2-chloro-3,4,5,6-tetrafluoropyridine,
2-chloro-6-fluoropyridine, 2-chloropyrazine,
3,6-dichloropyridazine, 2-chloro-1,3-thiazole,
2-chloro-5-nitro-1,3-thiazole,
2-chloro-4,5-dihydro-1,3-thiazole,
2-chloro-4,4-dimethyl-5-hydro-1,3-thiazole,
2-chloro-4,5-dihydro-4-methyl-1,3-thiazole,
2-chloro-4,5-dihydro-1,3-thiazine, 2-chloropyrimidine,
2-chloro-4,6-dimethylpyrimidine,
4-chloro-2,6-dimethylpyrimidine,
2,4,6-trichloro-1,3,5-triazine, and
2-chloro-4,6-dimethylthio-1,3,5-triazine.

The amount of halogenated nitrogen-containing heterocyclic compound used is usually 0.5 to 10 moles, preferably 0.8 to 2 moles, relative to 1 mole of alcohol derivative.

The base may include alkali metals such as sodium and potassium; alkyl lithium such as n-butyl lithium; alkali metal halides such as sodium hydride; alkali metal amides such as lithium amide; alkali metal hydroxides such as sodium hydroxide and potassium hydroxide; alkali metal carbonates such as sodium carbonate and potassium carbonate; and organic bases such as triethylamine. The amounts for their use are usually 1 to 2 moles, relative to 1 mole of halogenated nitrogen-containing heterocyclic compound.

The reaction is usually carried out in the presence of an organic solvent. The organic solvent may include single or mixed solvents selected from aprotic polar solvents such as N,N-dimethylformamide and dimethylsulfoxide; ether solvents such as tetrahydrofuran and dimethoxyethane; and aromatic hydrocarbon solvents such as toluene; or mixed solvents of these organic solvents and water. The amount of solvent used is not particularly limited. When mixed solvents of organic solvents and water are used, phase transfer catalysts such as benzyltriethyl ammonium chloride and tetra(n-butyl) ammonium bromide may be used so that the reaction can proceed more smoothly.

The reaction temperature is usually in the range of −80° C. to the reflux temperature of the reaction mixture, preferably in the range of 10° C. to the reflux temperature of the reaction mixture.

After completion of the reaction, for example, water and, if necessary, a water-insoluble organic solvent are added to the reaction mixture, followed by extraction, and the resulting organic layer is subjected to concentration to separate the desired (optically active) nitrogen-containing heterocyclic compound. The separated (optically active) nitrogen-containing heterocyclic compound may be further purified by an ordinary means of purification such as recrystallization, column chromatography and distillation.

The above alcohol derivative (4) is reacted with the above halogenated nitrogen-containing heterocyclic compound (5) to give a nitrogen-containing heterocyclic compound of formula (6):

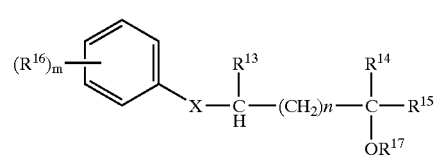

wherein X, $R^{13}$, $R^{14}$, $R^{15}$, $R^{16}$, $R^{17}$, X and n are as defined above.

In the above reaction, the use of alcohol derivatives of the above formula (4a) and (4'a) makes it possible to obtain nitrogen-containing heterocyclic compounds in which hydrogen atoms of hydroxyl groups in formula (4a) and (4'a) have been replaced by $R^{17}$.

The nitrogen-containing heterocyclic compound (6) thus obtained may include:

2-[1-methyl-2-(4-phenoxyphenoxy)ethoxy]pyridine,
2-[1-methyl-2-(3-phenoxyphenoxy)ethoxy]pyridine,
2-[1-methyl-2-[4-(3-methylphenoxy)phenoxy]ethoxy]pyridine,
2-[1-methyl-2-(2-methyl-4-phenoxyphenoxy)ethoxy]pyridine,
2-[1-methyl-2-[4-(2-fluorophenoxy)phenoxy]ethoxy]pyridine,
2-[1-methyl-2-[4-(3-fluorophenoxy)phenoxy]ethoxy]pyridine,
2-[1-methyl-2-[4-(4-fluorophenoxy)phenoxy]ethoxy]pyridine,
2-[1-methyl-2-[4-(3,5-difluorophenoxy)phenoxy]ethoxy]pyridine,
2-[1-methyl-2-[4-(3,5-dichlorophenoxy)phenoxy]ethoxy]pyridine,
2-[1-methyl-2-[4-(3-trifluoromethylphenoxy)phenoxy]ethoxy]pyridine,
2-[1-methyl-2-[4-(3-methoxyphenoxy)phenoxy]ethoxy]pyridine,
2-[1-methyl-2-(4-benzylphenoxy)ethoxy]pyridine,
2-[1-methyl-2-(4-phenoxythiophenoxy)ethoxy]pyridine,
6-methyl-2-[1-methyl-2-(4-phenoxyphenoxy)ethoxy]pyridine,
6-methyl-3-[1-methyl-2-(4-phenoxyphenoxy)ethoxy]pyridine,
5-nitro-2-[1-methyl-2-(4-phenoxyphenoxy)ethoxy]pyridine,
5-fluoro-2-[1-methyl-2-(4-phenoxyphenoxy)ethoxy]pyridine,
6-methoxy-2-[1-methyl-2-(4-phenoxyphenoxy)ethoxy]pyridine,
5-chloro-2-[1-methyl-2-(4-phenoxyphenoxy)ethoxy]pyridine,
3-chloro-2-[1-methyl-2-(4-phenoxyphenoxy)ethoxy]pyridine,
3-nitro-2-[1-methyl-2-(4-phenoxyphenoxy)ethoxy]pyridine,
3-[1-methyl-2-(4-phenoxyphenoxy)ethoxy]pyridine,
4-[1-methyl-2-(4-phenoxyphenoxy)ethoxy]pyridine,
3-chloro-5-trifluoromethyl-2-[1-methyl-2-(4-phenoxyphenoxy)ethoxy]pyridine,
5-fluoro-2-[1-methyl-2-[4-(3-fluorophenoxy)phenoxy]ethoxy]pyridine,
5-fluoro-2-[1-methyl-2-[4-(3,5-difluorophenoxy)phenoxy]ethoxy]pyridine,
2-[1-methyl-2-(4-phenoxyphenoxy)ethoxy]pyrazine,
6-chloro-3-[1-methyl-2-(4-phenoxyphenoxy)ethoxy]pyridazine,
2-[1-methyl-2-(4-phenoxyphenoxy)ethoxy]thiazoline,
2-[1-methyl-2-[4-(3-fluorophenoxy)phenoxy]ethoxy]thiazoline,
2-[1-methyl-2-[4-(3,5-difluorophenoxy)phenoxy]ethoxy]thiazoline,
5-nitro-2-[1-methyl-2-(4-phenoxyphenoxy)ethoxy]thiazoline,
2-[1-methyl-2-(4-phenoxyphenoxy)ethoxy]pyrimidine,
2-[1-methyl-2-[4-(3-fluorophenoxy)phenoxy]ethoxy]pyrimidine,
2-[1-methyl-2-[4-(3,5-difluorophenoxy)phenoxy]ethoxy]pyrimidine,
6-chloro-4-[1-methyl-2-(4-phenoxyphenoxy)ethoxy]pyrimidine,
6-methylthio-4-[1-methyl-2-(4-phenoxyphenoxy)ethoxy]pyrimidine,
4,6-dimethyl-2-[1-methyl-2-(4-phenoxyphenoxy)ethoxy]pyrimidine,
2,6-dimethyl-2-[1-methyl-2-(4-phenoxyphenoxy)ethoxy]pyrimidine,
2-[1-methyl-2-(4-phenoxyphenoxy)ethoxy]-3,5-dimethylthio-1,3,5-triazine,
2-[1-ethyl-2-(4-phenoxyphenoxy)ethoxy]pyridine,
2-[1-ethyl-2-(3-phenoxyphenoxy)ethoxy]pyridine,
2-[1-ethyl-2-[4-(3-methylphenoxy)phenoxy]ethoxy]pyridine,
2-[1-ethyl-2-(2-methyl-4-phenoxyphenoxy)ethoxy]pyridine,
2-[1-ethyl-2-[4-(2-fluorophenoxy)phenoxy]ethoxy]pyridine,
2-[1-ethyl-2-[4-(3-fluorophenoxy)phenoxy]ethoxy]pyridine,
2-[1-ethyl-2-[4-(4-fluorophenoxy)phenoxy]ethoxy]pyridine,
2-[1-ethyl-2-[4-(3,5-difluorophenoxy)phenoxy]ethoxy]pyridine,
2-[1-ethyl-2-[4-(3,5-dichlorophenoxy)phenoxy]ethoxy]pyridine,
2-[1-ethyl-2-[4-(3-trifluoromethylphenoxy)phenoxy]ethoxy]pyridine,
2-[1-ethyl-2-[4-(3-methoxyphenoxy)phenoxy]ethoxy]pyridine,
2-[1-ethyl-2-(4-benzylphenoxy)ethoxy]pyridine,
2-[1-ethyl-2-(4-phenoxythiophenoxy)ethoxy]pyridine,
6-methyl-2-[1-ethyl-2-(4-phenoxyphenoxy)ethoxy]pyridine,
6-methyl-3-[1-ethyl-2-(4-phenoxyphenoxy)ethoxy]pyridine,
5-nitro-2-[1-ethyl-2-(4-phenoxyphenoxy)ethoxy]pyridine,
5-fluoro-2-[1-ethyl-2-(4-phenoxyphenoxy)ethoxy]pyridine,
6-methoxy-2-[1-ethyl-2-(4-phenoxyphenoxy)ethoxy]pyridine,
5-chloro-2-[1-ethyl-2-(4-phenoxyphenoxy)ethoxy]pyridine,
3-chloro-2-[1-ethyl-2-(4-phenoxyphenoxy)ethoxy]pyridine,
3-nitro-2-[1-ethyl-2-(4-phenoxyphenoxy)ethoxy]pyridine,
3-[1-ethyl-2-(4-phenoxyphenoxy)ethoxy]pyridine,
4-[1-ethyl-2-(4-phenoxyphenoxy)ethoxy]pyridine,
3-chloro-5-trifluoromethyl-2-[1-ethyl-2-(4-phenoxyphenoxy)ethoxy]-pyridine,
5-fluoro-2-[1-ethyl-2-[4-(3-fluorophenoxy)phenoxy]ethoxy]pyridine, and
5-fluoro-2-[1-ethyl-2-[4-(3,5-difluorophenoxy)phenoxy]ethoxy]pyridine.

The above optically active alcohol derivative (4') is reacted with the above halogenated nitrogen-containing heterocyclic compound (5) to give an optically active nitrogen-containing heterocyclic compound of formula (6'):

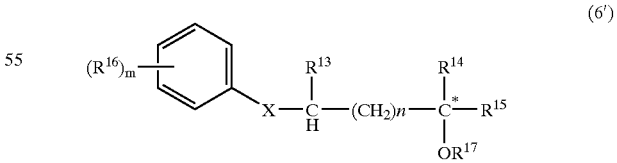

(6')

(hereinafter abbreviated as optically active nitrogen-containing heterocyclic compound (6'))

wherein $R^{11}$, $R^{12}$, $R^{13}$, $R^{14}$, $R^{15}$, X, Y, n and * are as defined above.

The optically active nitrogen-containing heterocyclic compound (6') thus obtained may include:

optically active 2-[1-methyl-2-(4-phenoxyphenoxy)ethoxy]pyridine,
optically active 2-[1-methyl-2-(3-phenoxyphenoxy)ethoxy]pyridine,
optically active 2-[1-methyl-2-[4-(3-methylphenoxy)phenoxy]ethoxy]-pyridine,
optically active 2-[1-methyl-2-(4-phenoxy-2-methylphenoxy)ethoxy]-pyridine,
optically active 2-[1-methyl-2-[4-(2-fluorophenoxy)phenoxy]ethoxy]-pyridine,
optically active 2-[1-methyl-2-[4-(3-fluorophenoxy)phenoxy]ethoxy]-pyridine,
optically active 2-[1-methyl-2-[4-(4-fluorophenoxy)phenoxy]ethoxy]-pyridine,
optically active 2-[1-methyl-2-[4-(3,5-difluorophenoxy)phenoxy]ethoxy]pyridine,
optically active 2-[1-methyl-2-[4-(3,5-dichlorophenoxy)phenoxy]ethoxy]pyridine,
optically active 2-[1-methyl-2-[4-(3-trifluoromethylphenoxy)phenoxy]ethoxy]pyridine,
optically active 2-[1-methyl-2-[4-(3-methoxyphenoxy)phenoxy]ethoxy]pyridine,
optically active 2-[1-methyl-2-(4-benzylphenoxy)ethoxy]pyridine,
optically active 2-[1-methyl-2-(4-phenoxythiophenoxy)ethoxy]pyridine,
optically active 6-methyl-2-[1-methyl-2-(4-phenoxyphenoxy)ethoxy]-pyridine,
optically active 6-methyl-3-[1-methyl-2-(4-phenoxyphenoxy)ethoxy]-pyridine,
optically active 5-nitro-2-[1-methyl-2-(4-phenoxyphenoxy)ethoxy]-pyridine,
optically active 5-fluoro-2-[1-methyl-2-(4-phenoxyphenoxy)ethoxy]-pyridine,
optically active 6-methoxy-2-[1-methyl-2-(4-phenoxyphenoxy)ethoxy]pyridine,
optically active 5-chloro-2-[1-methyl-2-(4-phenoxyphenoxy)ethoxy]-pyridine,
optically active 3-chloro-2-[1-methyl-2-(4-phenoxyphenoxy)ethoxy]-pyridine,
optically active 3-nitro-2-[1-methyl-2-(4-phenoxyphenoxy)ethoxy]-pyridine,
optically active 3-[1-methyl-2-(4-phenoxyphenoxy)ethoxy]pyridine,
optically active 4-[1-methyl-2-(4-phenoxyphenoxy)ethoxy]pyridine,
optically active 3-chloro-5-trifluoromethyl-2-[1-methyl-2-(4-phenoxyphenoxy)ethoxy]pyridine,
optically active 5-fluoro-2-[1-methyl-2-[4-(3-fluorophenoxy)phenoxy]-ethoxy]pyridine,
optically active 5-fluoro-2-[1-methyl-2-[4-(3,5-difluorophenoxy)phenoxy]ethoxy]pyridine,
optically active 2-[1-methyl-2-(4-phenoxyphenoxy)ethoxy]pyrazine,
optically active 6-chloro-3-[1-methyl-2-(4-phenoxyphenoxy)ethoxy]-pyridazine,
optically active 2-[1-methyl-2-(4-phenoxyphenoxy)ethoxy]thiazoline,
optically active 2-[1-methyl-2-[4-(3-fluorophenoxy)phenoxy]ethoxy]-thiazoline,
optically active 2-[1-methyl-2-[4-(3,5-difluorophenoxy)phenoxy]ethoxy]thiazoline,
optically active 5-nitro-2-[1-methyl-2-(4-phenoxyphenoxy)ethoxy]-thiazoline,
optically active 2-[1-methyl-2-(4-phenoxyphenoxy)ethoxy]pyrimidine,
optically active 2-[1-methyl-2-[4-(3-fluorophenoxy)phenoxy]ethoxy]-pyrimidine,
optically active 2-[1-methyl-2-[4-(3,5-difluorophenoxy)phenoxy]ethoxy]pyrimidine,
optically active 6-chloro-4-[1-methyl-2-(4-phenoxyphenoxy)ethoxy]-pyrimidine,
optically active 6-methylthio-4-[1-methyl-2-(4-phenoxyphenoxy)ethoxy]pyrimidine,
optically active 4,6-dimethyl-2-[1-methyl-2-(4-phenoxyphenoxy)ethoxy]pyrimidine,
optically active 2,6-dimethyl-2-[1-methyl-2-(4-phenoxyphenoxy)ethoxy]pyrimidine,
optically active 2-[1-methyl-2-(4-phenoxyphenoxy)ethoxy]-3,5-di-methylthio-1,3,5-triazine,
optically active 2-[1-ethyl-2-(4-phenoxyphenoxy)ethoxy]pyridine,
optically active 2-[1-ethyl-2-(3-phenoxyphenoxy)ethoxy]pyridine,
optically active 2-[1-ethyl-2-[4-(3-methylphenoxy)phenoxy]ethoxy]-pyridine,
optically active 2-[1-ethyl-2-(4-phenoxy-2-methylphenoxy)ethoxy]-pyridine,
optically active 2-[1-ethyl-2-[4-(2-fluorophenoxy)phenoxy]ethoxy]pyridine,
optically active 2-[1-ethyl-2-[4-(3-fluorophenoxy)phenoxy]ethoxy]pyridine,
optically active 2-[1-ethyl-2-[4-(4-fluorophenoxy)phenoxy]ethoxy]pyridine,
optically active 2-[1-ethyl-2-[4-(3,5-difluorophenoxy)phenoxy]ethoxy]pyridine,
optically active 2-[1-ethyl-2-[4-(3,5-dichlorophenoxy)phenoxy]ethoxy]pyridine,
optically active 2-[1-ethyl-2-[4-(3-trifluoromethylphenoxy)phenoxy]-ethoxy]pyridine,
optically active 2-[1-ethyl-2-[4-(3-methoxyphenoxy)phenoxy]ethoxy]-pyridine,
optically active 2-[1-ethyl-2-(4-benzylphenoxy)ethoxy]pyridine,
optically active 2-[1-ethyl-2-(4-phenoxythiophenoxy)ethoxy]pyridine,
optically active 6-methyl-2-[1-ethyl-2-(4-phenoxyphenoxy)ethoxy]-pyridine,
optically active 6-methyl-3-[1-ethyl-2-(4-phenoxyphenoxy)ethoxy]-pyridine,
optically active 5-nitro-2-[1-ethyl-2-(4-phenoxyphenoxy)ethoxy]pyridine,
optically active 5-fluoro-2-[1-ethyl-2-(4-phenoxyphenoxy)ethoxy]pyridine,
optically active 6-methoxy-2-[1-ethyl-2-(4-phenoxyphenoxy)ethoxy]-pyridine,
optically active 5-chloro-2-[1-ethyl-2-(4-phenoxyphenoxy)ethoxy]pyridine,
optically active 3-chloro-2-[1-ethyl-2-(4-phenoxyphenoxy)ethoxy]pyridine,
optically active 3-nitro-2-[1-ethyl-2-(4-phenoxyphenoxy)ethoxy]pyridine,
optically active 3-[1-ethyl-2-(4-phenoxyphenoxy)ethoxy]pyridine,
optically active 4-[1-ethyl-2-(4-phenoxyphenoxy)ethoxy]pyridine,
optically active 3-chloro-5-trifluoromethyl-2-[1-ethyl-2-(4-phenoxyphenoxy)ethoxy]pyridine,
optically active 5-fluoro-2-[1-ethyl-2-[4-(3-fluorophenoxy)phenoxy]-ethoxy]pyridine, and
optically active 5-fluoro-2-[1-ethyl-2-[4-(3,5-difluorophenoxy)phenoxy]ethoxy]pyridine.

EXAMPLES

The present invention will be further illustrated by reference to the following examples; however, the present invention is not limited to these examples. The yields were calculated from the results of analysis by high performance liquid chromatography. The optical purity of optically active alcohol derivatives and the optical purity of optically active nitrogen-containing heterocyclic compounds were calculated from the results of analysis by high performance liquid chromatography using optically active columns (CHIRALCEL OD: available from DAICEL CHEMICAL INDUSTRIES, LTD.) and optically active columns (CHIRALCEL OJ-H: available from DAICEL CHEMICAL INDUSTRIES, LTD.), respectively.

Example 1

A nitrogen-purged 200-mL separable flask was charged with 404 mg of (R,R)-(−)-N,N'-bis(3,5-di-tert-butylsalicylidene)-1,2-cyclohexanediamino cobalt (III) 4-phenoxyphenolate and 10 mL of tert-butyl methyl ether, to which 147 mg of tetraisopropoxy titanium was added, and the mixture was stirred at room temperature for 1 hour to prepare a catalyst solution (the color of the catalyst solution changed from brown to slightly greenish brown). To the catalyst solution were added 9.41 g of 4-phenoxyphenol and 10 mL of tert-butyl methyl ether, and the mixture was cooled to the internal temperature of 5° C., after which 13.2 g of propylene oxide was added dropwise over 30 minutes. The mixture was kept stirred at the same temperature for 8 hours to achieve the reaction, followed by addition of water and extraction with ethyl acetate. From the resulting organic layer, the solvent was distilled out to give a solid substance containing (S)-(+)-1-(4-phenoxyphenoxy)-2-propanol.

The yield of (S)-(+)-1-(4-phenoxyphenoxy)-2-propanol: 98% (based on 4-phenoxyphenol); optical purity: 98% e.e.

To a suspension prepared by suspending 1.14 g of sodium hydride (60 wt % oil suspension) in 40 mL of N,N-dimethylformamide was slowly added under ice cooling a solution prepared by dissolving the solid substance (pure content: 5.34 g) obtained above in 20 g of N,N-dimethylformamide, followed by keeping stirred at room temperature for 1 hour. Then 3.64 g of 2-chloropyridine was added, and the mixture was stirred at the internal temperature of 60° C. for 10 hours to achieve the reaction. Then ice water was poured into the reaction mixture, which was extracted three times with ethyl acetate. The resulting organic layer was concentrated to give a solid substance containing (S)-(+)-2-[1-methyl-2-(4-phenoxyphenoxy)ethoxy]pyridine.

The yield of (S)-(+)-2-[1-methyl-2-(4-phenoxyphenoxy)ethoxy]pyridine: 91% (based on (S)-(+)-1-(4-phenoxyphenoxy)-2-propanol); and optical purity: 98% e.e.

Example 2

A nitrogen-purged 50-mL Schlenk's tube was charged with 81 mg of (R,R)-(−)-N,N-bis(3,5-di-tert-butylsalicylidene)-1,2-cyclohexanediamino cobalt (III) 4-phenoxyphenolate and 1 mL of tert-butyl methyl ether, to which 13 mg of anhydrous aluminum chloride and 1 g of molecular sieves 3A were added, and the mixture was stirred at room temperature for 1 hour to prepare a catalyst solution. With the lapse of time, the color of the catalyst solution changed from brown to dark green. To the dark green catalyst solution were added 960 mg of 4-phenoxyphenol and 1.47 g of propylene oxide, and the mixture was stirred at room temperature for 20 hours to achieve the reaction. After completion of the reaction, tert-butyl methyl ether was distilled out to give an oily substance containing (S)-(+)-1-(4-phenoxyphenoxy)-2-propanol.

The yield of (S)-(+)-1-(4-phenoxyphenoxy)-2-propanol: 82% (based on 4-phenoxyphenol); and optical purity: 92% e.e.

The resulting oily substance containing (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 3

In Example 2, 0.1 mL of a diethyl aluminum chloride/hexane solution was used in place of anhydrous aluminum chloride, and the color of the catalyst solution changed from brown to dark green by the addition of a diethyl aluminum chloride/hexane solution. Then 4-phenoxyphenol and propylene oxide were added to the dark green catalyst solution to achieve the reaction in the same manner as described in Example 2. Thus (S)-(+)-1-(4-phenoxyphenoxy)-2-propanol was obtained in 72% yield and the optical purity was 87% e.e.

The resulting (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 4

In Example 2, 26 mg of tri-tert-butoxy aluminum was used in place of anhydrous aluminum chloride, and the color of the catalyst solution changed from brown to slightly greenish brown by the addition of tri-tert-butoxy aluminum. Then 4-phenoxyphenol and propylene oxide were added to the slightly greenish brown catalyst solution to achieve the reaction in the same manner as described in Example 2. Thus (S)-(+)-1-(4-phenoxyphenoxy)-2-propanol was obtained in 68% yield and the optical purity was 87% e.e.

The resulting (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 5

In Example 2, 16 mg of tri-tert-ethoxy aluminum was used in place of anhydrous aluminum chloride, and the color of the catalyst solution changed from brown to slightly greenish brown by the addition of tri-tert-ethoxy aluminum. Then 4-phenoxyphenol and propylene oxide were added to the slightly greenish brown catalyst solution to achieve the reaction in the same manner as described in Example 2. Thus (S)-(+)-1-(4-phenoxyphenoxy)-2-propanol was obtained in 83% yield and the optical purity was 90% e.e.

The resulting (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 6

In Example 2, 29 mg of tetraisopropoxy titanium was used in place of anhydrous aluminum chloride, and the color of the catalyst solution changed from brown to slightly greenish brown by the addition of tetraisopropoxy titanium. Then 4-phenoxyphenol and propylene oxide were added to the slightly greenish brown catalyst solution to achieve the reaction in the same manner as described in Example 2. Thus (S)-(+)-1-(4-phenoxyphenoxy)-2-propanol was obtained in 84% yield and the optical purity was 95% e.e.

The resulting (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 7

In Example 2, the amount of (R,R)-(−)-N,N'-bis(3,5-di-tert-butylsalicylidene)-1,2-cyclohexanediamino cobalt (III) 4-phenoxyphenolate used was changed to 41 mg, and 15 mg of tetraisopropoxy titanium was used in place of anhydrous aluminum chloride, and the color of the catalyst solution changed from brown to slightly greenish brown by the addition of tetraisopropoxy titanium. Then 4-phenoxyphenol and propylene oxide were added to the slightly greenish brown catalyst solution to achieve the reaction in the same manner as described in Example 2. Thus (S)-(+)-1-(4-phenoxyphenoxy)-2-propanol was obtained in 77% yield and the optical purity was 94% e.e.

The resulting (S)-(+)-1-(4-phenoxyphenoxy)-2-propanol was reacted with 2-chloropyridine in the same manner as described in Example 1 to give (S)-(+)-2-[1-methyl-2-(4-phenoxyphenoxy)ethoxy]pyridine.

Example 8

A nitrogen-purged 50-mL Schlenk's tube was charged with 404 mg of (R,R)-(−)-N,N-bis(3,5-di-tert-butylsalicylidene)-1,2-cylcohexanediamino cobalt (III) 4-phenoxyphanolate and 10 mL of tert-butyl ethyl ether, and the IR spectrum of the reaction mixture was measured. Then 147 mg of tetraisopropoxy titanium was added, and the color of the reaction mixture was changed from brown to slightly greenish brown. The peaks at 752 $cm^{-1}$ and 956 $cm^{-1}$ appeared in addition to the peaks from (R,R)-(−)-N,N-bis(3,5-ditert-butylsalicylidene)-1,2-cyclohexanediamino cobalt (III) 4-phenoxyphenolate, tert-butyl methyl ether and tetraisopropoxy titanium.

Comparative Example 1

A nitrogen-purged 50-mL Schlenk's tube was charged with 202 mg of (R,R)-(−)-N,N'-bis(3,5-di-tert-butylsalicylidene)-1,2-cyclohexanediamino cobalt (III) 4-phenoxyphenolate, 1 g of molecular sieves 3A, 960 mg of 4-phenoxyphenol and 1.47 g of propylene oxide, and the mixture was stirred at room temperature for 20 hours to achieve the reaction. After completion of the reaction, the solvent was distilled out to give an oily substance containing (S)-(+)-1-(4-phenoxyphenoxy)-2-propanol. The oily substance was analyzed by high performance liquid chromatography in the same manner as described in Example 1 to reveal that the yield of (S)-(+)-1-(4-phenoxyphenoxy)-2-propanol was 14% (based on 4-phenoxyphenol) and the optical purity was 77% e.e.

Comparative Example 2

A nitrogen-purged 50-mL Schlenk's tube was charged with 960 mg of 4-phenoxyphenol and 1 mL of tert-butyl ethyl ether, to which 13 mg of anhydrous aluminum chloride, 1 g of molecular sieves 3A and 1.47 g of propylene oxide were added, and the mixture was stirred at room temperature for 20 hours to achieve the reaction. After completion of the reaction, tert-butyl methyl ether was distilled out to give an oily substance. The oily substance was analyzed by high performance liquid chromatography to reveal that the main component was 4-phenoxyphenol and the recovery of 4-phenoxyphenol was 93%.

Example 9

A nitrogen-purged 200-mL separable flask was charged with 170 mg of N,N'-bis(salicylidene)-1,2-diphenylethylenediamino cobalt (III) 4-phenoxyphenolate and 10 mL of tert-butyl methyl ether, to which 733 mg of tetraisopropoxy titanium was added, and the mixture was stirred at room temperature for 1 hour to prepare a catalyst solution (the color of the catalyst solution changed from brown to slightly greenish brown). To the catalyst solution were added 9.41 g of 4-phenoxyphenol and 10 mL of tert-butyl methyl ether, and the mixture was cooled to the internal temperature of 5° C. To this was added dropwise 6.6 g of propylene oxide over 30 minutes, and the mixture was then stirred at 5° C. for 8 hours to achieve the reaction. After completion of the reaction, tert-butyl methyl ether was distilled out to give an oily substance containing 1-(4-phenoxyphenoxy)-2-propanol. The oily substance was quantitated by high performance liquid chromatography (hereinafter abbreviated as LC) to reveal that the yield of 1-(4-phenoxyphenoxy)-2-propanol was 93% (based on 4-phenoxyphenol) and isomer ratio 1 was 0.001.

Isomer ratio 1 was calculated by the following equation:

Isomer ratio 1=[$LC$ area value of 2-(4-phenoxyphenoxy)-1-propanol]/[$LC$ area value of 2-(4-phenoxyphenoxy)-1-propanol+$LC$ area value of 1-(4-phenoxyphenoxy)-2-propanol]

To the resulting oily substance (pure content: 10.5 g) were added 6.5 g of 2-chloropyridine and 3.5 g of sodium hydroxide (granular), followed by mixing with stirring at the internal temperature of 100° C. Then azeotropic dehydration was carried out at the internal temperature of 150° C., operation pressure of 70 Torr (corresponding to 9.3 kPa) to achieve the reaction for 3 hours. Then the remaining 2-chloropyridine was distilled out at the internal temperature of 157° C., operation pressure of 10 Torr (corresponding to 1.3 kPa), followed by cooling. To the reaction mixture were added water and toluene, and the mixture was filtered through Celite. The filtrate was extracted with toluene, and the resulting organic layer was concentrated to give 2-[1-methyl-2-(4-phenoxyphenoxy)ethoxy]pyridine. Yield: 90%. Isomer ratio 2 was 0.001.

Isomer ratio 2 was calculated by the following equation:

Isomer ratio 2={$LC$ area value of 2-[1-methyl-2-(4-phenoxyphenoxy)ethoxy]pyridine}/{$LC$ area value of 2-[1-methyl-2-(4-phenoxyphenoxy)ethoxy]pyridine+$LC$ area value of 2-[2-methyl-2-(4-phenoxyphenoxy)ethoxy]pyridine}

Example 10

A nitrogen-purged 50-mL Schlenk's tube was charged with 26 mg of N,N'-bis(salicylidene)-ethylenediamine cobalt (III) 4-phenoxyphenolate and 1 mL of tert-butyl methyl ether, to which 74 mg of tetraisopropoxy titanium was added, and the mixture was stirred at room temperature for 1 hour to prepare a catalyst solution. To the catalyst solution were added 960 mg of 4-phenoxyphenol and 1.47 g of propylene oxide, and the mixture was then stirred at room temperature for 20 hours to achieve the reaction. After completion of the reaction, tert-butyl methyl ether was distilled out to give an oily substance containing 1-(4-phenoxyphenoxy)-2-propanol. Yield: 92% (based on 4-phenoxyphenol). Isomer ratio 1=0.003 (isomer ratio 1 was calculated by the same equation as described above in Example 9).

The resulting oily substance containing 1-(4-phenoxyphenoxy)-2-propanol is reacted with 2-chloropyridine in the same manner as described in Example 9 to give 2-[1-methyl-2-(4-phenoxyphenoxy)ethoxy]pyridine.

Example 11

In Example 9, the reaction was carried out in the same manner as described in Example 9, except that 17 mg of N,N'-bis(salicylidene)-1,2-diphenylethylenediamino cobalt (III) 4-phenoxyphenolate was used in place of 26 mg of N,N'-bis(salicylidene)-ethylenediamino cobalt (III) 4-phenoxyphenolate and the amount of tert-butyl methyl ether used for the preparation of a catalyst was changed to 2 mL, 1-(4-phenoxyphenoxy)-2-propanol was obtained in 95% yield and isomer ratio 1=0.003 (isomer ratio 1 was calculated by the same equation as described above in Example 9).

The resulting oily substance containing 1-(4-phenoxyphenoxy)-2-propanol is reacted with 2-chloropyridine in the same manner as described in Example 9 to give 2-[1-methyl-2-(4-phenoxyphenoxy)ethoxy]pyridine.

INDUSTRIAL APPLICABILITY

According to the present invention, novel (asymmetric) complex catalysts obtained by reaction of (optically active) metal complexes with Lewis acids exhibit high catalytic activity in the reaction of cyclic ether compounds with phenol derivatives; therefore, it is possible to produce (optically active) alcohol derivatives in an industrially advantageous manner by reacting cyclic ether compounds with phenol derivatives in the presence of these (asymmetric) complex catalysts, and it is possible to obtain (optically active) nitrogen-containing heterocyclic compounds in an industrially advantageous manner by reacting these resulting (optically active) alcohol derivatives with halogenated nitrogen-containing heterocyclic compounds in the presence of a base.

What is claimed is:

1. A complex catalyst comprising, as components, a Lewis acid and
a metal complex of formula (1):

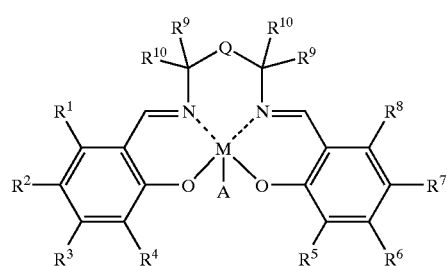

wherein $R^1$, $R^2$, $R^3$, $R^4$, $R^5$, $R^6$, $R^7$ and $R^8$ are the same or different and are independently hydrogen, halogen, alkyl, alkenyl, alkynyl, alkoxy, haloalkyl, haloalkoxy, hydroxyl, nitro, amino, carbamoyl, carboxyl, substituted or unsubstituted aryl, or silyl; or two adjacent groups of $R^1$, $R^2$, $R^3$, $R^4$, $R^5$, $R^6$, $R^7$ and $R^8$ are combined together to represent a naphthalene ring by forming a ring together with a benzene ring to which they are attached;

one of $R^9$ and $R^{10}$ is hydrogen and the other is phenyl or naphthyl optionally substituted with at least one selected from the group consisting of alkyl of 1 to 4 carbon atoms, alkoxy of 1 to 4 carbon atoms, haloalkyl, haloalkoxy and halogen; or either one pair of $R^9$ and $R^{10}$ attached to the different carbon atoms are combined together at their ends to form a tetramethylene linkage and the other pair are hydrogen atoms;

Q is a single bond or alkylene of 1 to 4 carbon atoms; or Q is combined with $R^9$ and $R^{10}$ to represent 1,1'-binaphthyl attached to the nitrogen atoms at 2 and 2' positions;

M is cobalt ion, a chromium ion or a manganese ion; and
A is a balancing counter ion or ligand,
wherein the Lewis acid is selected from the group consisting of an aluminum halide, a dialkyl aluminum halide, a trialkoxy aluminum, a titanium halide, a tetraalkoxy titanium, a boron halide and a zinc halide.

2. A complex catalyst according to claim 1, wherein the metal complex is an optically active metal complex of formula (1'):

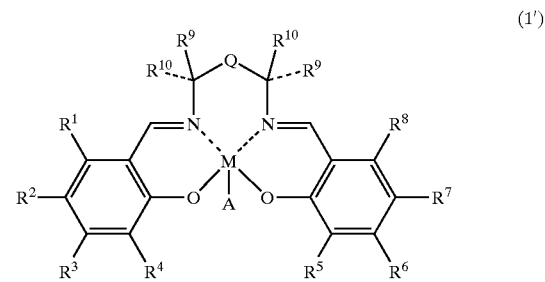

wherein $R^1$, $R^2$, $R^3$, $R^4$, $R^5$, $R^6$, $R^7$, $R^8$, $R^9$, $R^{10}$, M, A and Q are as defined in formula (1).

3. A complex catalyst according to claim 1, wherein Q is a single bond.

4. A complex catalyst according to claim 2, wherein Q is a single bond.

5. A process for the production of a metal complex catalyst according to claim 1, characterized in that a metal complex of formula (1) is reacted with a Lewis acid selected from the group consisting of an aluminum halide, a dialkyl aluminum halide, a trialkoxy aluminum, a titanium halide, a tetraalkoxy titanium, a boron halide and a zinc halide.

6. A process for the production of an alcohol derivative of the following formula (4):

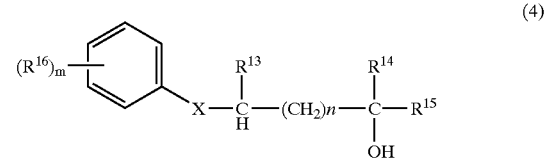

wherein $R^{13}$, $R^{14}$, $R^{15}$, $R^{16}$, X, m and n are as defined below, characterized in that a cyclic ether compound of formula (2):

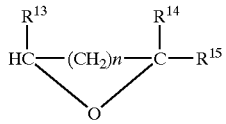

(2)

wherein $R^{13}$ is hydrogen; $R^{14}$ is hydrogen or alkyl; or $R^{13}$ and $R^{14}$ are combined together to represent alkylene of 2 to 6 carbon atoms; $R^5$ is alkyl, aryl or aralkyl; where the alkyl, aryl and aralkyl groups may optionally have a substituent(s); and n is 0 or 1, is reacted with a phenol derivative of the following formula (3):

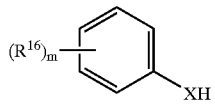

(3)

wherein X is oxygen or sulfur; $R^{16}$'s are the same or different and are independently hydrogen, halogen, nitro, alkyl of 1 to 6 carbon atoms, alkoxy of 1 to 6 carbon atoms, phenylthio, benzyl or phenoxy; where the alkyl group of 1 to 6 carbon atoms, the alkoxy group of 1 to 6 carbon atoms, the phenylthio, benzyl or phenoxy group may optionally be substituted with alkyl of 1 to 4 carbon atoms, alkoxy of 1 to 4 carbon atoms, haloalkyl of 1 to 4 carbon atoms, haloalkoxy of 1 to 4 carbon atoms, or halogen; and m is an integer of 0 to 5, in the presence of a complex catalyst according to claim 1.

7. A production process according to claim 8, comprising the further step of reacting the alcohol derivative of formula (4) with a halogenated nitrogen-containing heterocyclic compound of formula (5):

$$Z—R^{17}$$ (5)

wherein Z is halogen and $R^{17}$ is pyridyl, pyridazinyl, pyrimidinyl, pyrazinyl, triazinyl, 2-thiazolyl or dihydro-2-thiazolyl; wherein these groups may optionally have one or more than one substituent selected from the group consisting of halogen, alkyl of 1 to 4 carbon atoms, alkoxy of 1 to 4 carbon atoms, alkylthio of 1 to 4 carbon atoms, trifluoromethyl and nitro, to give a nitrogen-containing heterocyclic compound of formula (6):

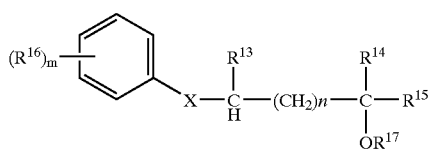

(6)

wherein X, $R^{13}$, $R^{14}$, $R^{15}$, $R^{16}$, m and n are as defined in claim 6.

8. A process for the production of an optically active alcohol derivative of the following formula (4):

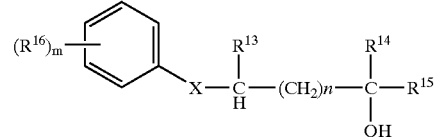

(4)

wherein $R^{13}$, $R^{14}$, $R^{15}$, $R^{16}$, X, m and n are as defined below and * indicates an asymmetric carbon atom, characterized in that a cyclic ether compound of formula (2):

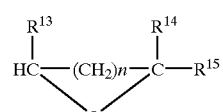

(2)

wherein $R^{13}$ is hydrogen; $R^{14}$ is hydrogen or alkyl; or $R^{13}$ and $R^{14}$ are combined together to represent alkylene of 2 to 6 carbon atoms; $R^{15}$ is alkyl, aryl or aralkyl; where the alkyl, aryl or aralkyl group may optionally have a substituent(s); and n is 0 or 1, is reacted with a phenol derivative of the following formula (3):

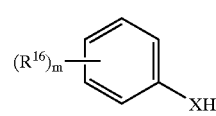

(3)

wherein X is oxygen or sulfur; $R^{16}$'s are the same or different and are independently hydrogen, halogen, nitro, alkyl of 1 to 6 carbon atoms, alkoxy of 1 to 6 carbon atoms, phenylthio, benzyl or phenoxy; wherein the alkyl group of 1 to 6 carbon atoms, the alkoxy group of 1 to 6 carbon atoms, the phenylthio, benzyl or phenoxy group may optionally be substituted with alkyl of 1 to 4 carbon atoms, alkoxy of 1 to 4 carbon atoms, haloalkyl of 1 to 4 carbon atoms, haloalkoxy of 1 to 4 carbon atoms, or halogen; and m is an integer of 0 to 5, in the presence of an asymmetric complex catalyst according to claim 2.

9. A production process according to claim 8, comprising the further step of reacting the optically active alcohol derivative of formula (4') with a halogenated nitrogen-containing heterocyclic compound of formula (5):

$$Z—R^{17}$$ (5)

wherein Z is halogen and $R^{17}$ is pyridyl, pyridazinyl, pyrimidinyl, pyrazinyl, triazinyl, 2-thiazolyl or dihydro-2-thiazolyl; wherein these groups may optionally have one to two substituents selected from the group consisting of halogen, alkyl of 1 to 4 carbon atoms, alkoxy of 1 to 4 carbon atoms, alkylthio of 1 to 4 carbon atoms, trifluoromethyl and nitro in the presence of a base to give an optically active nitrogen-containing heterocyclic compound of formula (6'):

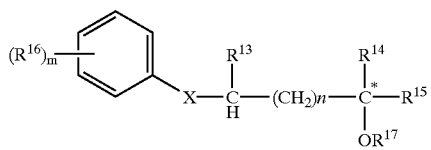
(6')
wherein $R^{13}$, $R^{14}$, $R^{15}$, X, m, n and * are as defined in claim 8.
10. A production process according to claim 7 or 9, wherein $R^{13}$ is hydrogen; $R^{14}$ is hydrogen; $R^{15}$ is methyl or ethyl; $R^{16}$ is hydrogen, halogen, alkyl of 1 to 4 carbon atoms, alkoxy of 1 to 4 carbon atoms, or trifluoromethyl; and n is an integer of 0 to 1.
* * * * *